US005525484A

United States Patent [19]
Alford et al.

[11] Patent Number: 5,525,484
[45] Date of Patent: Jun. 11, 1996

[54] RECOMBINANT DNA MEANS AND METHOD FOR PRODUCING RENNIN, PRORENIN AND PRE-PRORENNIN

[75] Inventors: Bernadette L. Alford, Ashland; Jen-I Mao, Bedford; Donald T. Moir, Waltham; Alison Taunton-Rigby, Lincoln; Gerald F. Vovis, Waltham, all of Mass.

[73] Assignee: Genome Therapeutics Corp., Waltham, Mass.

[21] Appl. No.: 58,939

[22] Filed: Jun. 5, 1987

Related U.S. Application Data

[63] Continuation of Ser. No. 640,514, Aug. 13, 1984, abandoned, which is a continuation-in-part of Ser. No. 325,481, Dec. 1, 1981, Pat. No. 4,666,847, which is a continuation-in-part of Ser. No. 225,717, Jan. 16, 1981, abandoned.

[51] Int. Cl.$^6$ .................... C12P 21/06; C12N 15/00; C12N 15/12
[52] U.S. Cl. .............. 435/69.1; 435/172.3; 435/226; 435/243; 435/252.3; 435/252.33; 435/254.2; 435/254.11; 435/254.21; 435/320.1; 536/23.5; 935/14; 935/68; 935/69; 935/72; 935/73
[58] Field of Search ................. 435/212, 213, 435/72.3, 253, 69.1, 243, 320.1, 254.11, 252.3, 252.33, 254.2, 254.21, 172.3, 226; 536/27, 23.5; 530/324; 935/10, 14, 18, 23, 37, 56, 60, 61, 68, 69, 73, 72

[56] References Cited

U.S. PATENT DOCUMENTS

| | | | |
|---|---|---|---|
| 4,136,201 | 1/1979 | Feldman | 435/226 |
| 4,322,499 | 3/1982 | Baxter et al. | 435/252.33 |
| 4,332,892 | 6/1982 | Ptashne et al. | 435/68 |
| 4,338,397 | 7/1982 | Gilbert et al. | 435/68 |
| 4,349,629 | 9/1982 | Carey et al. | 435/172.3 |
| 4,370,417 | 1/1983 | Hung et al. | 435/212 |
| 4,387,162 | 6/1983 | Aigle et al. | 435/172.3 |

FOREIGN PATENT DOCUMENTS

| | | |
|---|---|---|
| 0001931 | 5/1979 | European Pat. Off. . |
| 0009930 | 4/1980 | European Pat. Off. . |
| 0036776 | 9/1981 | European Pat. Off. . |
| 0037687 | 10/1981 | European Pat. Off. . |
| 0054330 | 6/1982 | European Pat. Off. . |
| 0057350 | 8/1982 | European Pat. Off. . |
| 0068691 | 1/1983 | European Pat. Off. . |
| 0073029 | 2/1983 | European Pat. Off. . |
| 0077109 | 4/1983 | European Pat. Off. . |
| 2069503 | 8/1981 | United Kingdom . |
| 2100737 | 1/1983 | United Kingdom . |
| 2121048 | 12/1983 | United Kingdom . |

OTHER PUBLICATIONS

Foltman, in *Methods in Enzymology*, vol. 19, pp. 431–436 (1970) Academic Press, NY.
Houghton et al, Nucl. Acids Res. 8 (May 10, 1980) 1913.
Uchiyama et al, Agric. Biol. Chem. 44(6) 1373 (Jun. 1980).
Talmadge et al Proc. Nat'l Acad Sci USA 77(7) 1980; 3988–92.
Ernst–L. Winnacker, "Gene und Klone", Vevlag Chemie, pp. 257–258 (1984).
Guarente et al, Chem. Abstr. 93: 65844t (1980).
Higuchi et al, Proc. Natl. Acad. Sci. USA 73: 3146 (1976).
Rose et al, Proc. Natl. Acad. Sci. USA 78: 2460 (1981).
Guarente et al, Proc. Natl. Acad. Sci. USA 78: 2199 (1981).
Old et al, Principles of Gene Manipulation, Blackwell Scientific Publications 59–88 (1980).
Glover, Genetic Engineering Cloning DNA, Chapman and Hall 36–48 (1980).
Maniatis et al, Molcular Cloning, A Laboratory Manual, Cold Spring Harbor Laboratory, Cold Spring Harbor, NY, pp. iii, iv, 211–246, 309–361, and 403–433 (1982).
Goodman et al, Methods in Enzymol. 68: 75–90 (1979).
Maxam et al, Proc. Natl. Acad. Sci. USA 74: 560 (1977).
Guarente et al, Cell 20: 543 (1980).
Maxam et al, Methods Enzymol. 65: 499 (1980).
Dulbecco, Microbiological Reviews 43: 443 (1979).
Ehrlich et al, TIBS Nov. 1978, pp. 259–261.
Old et al, Principle of Gene Manipulation: An Introduction to Genetic Engineering, Studies in Microbiology, vol. 2, pp. 104–105 (1981).
Foltman, Prochymosin and Chymosin (Prorennin and Rennin) in *Methods in Enzymology* vol. 19, pp. 421–436 (1970) Academic Press, N.Y.
Moir, D., et al. Molecular Cloning and Characterization of double–stranded cDNA coding for bovine chymosin, Gene 19:127–138 (1982).
Foltman, B. Milk Proteins 2:217–254 (1971).
Chang, et al., "Phenotypic expression in *E. coli* of DNA Sequence coding for mouse dihydrofolate reductase", Nature 275:617–624 (1978).
Goeddel, D. V., et al., "Direct expression in *Escherichia coli* of a DNA sequence coding for human growth hormone," Nature 281:544–548 (1979).
Uchiyama, H., et al., "Purification of prorennin mRNA and its translation in Vitro," Agric. Biol. Chem. 44:1373–1381 (1980).
Nishimori, K., et al., "Cloning in *Escherichia coli* of the structural gene of prorennin, the precursor of calf milk–clotting enzyme rennin," J. Biochem. 90:901–904 (1981).
Nishimori, K., et al., "Nucleotide sequence of calf prorennin cDNA cloned in *Escherichia coli*," J. Biochem. 91:1085–1088 (1982).

(List continued on next page.)

*Primary Examiner*—James Martinell
*Attorney, Agent, or Firm*—Wolf, Greenfield & Sacks

[57] ABSTRACT

Living cells containing genetic material derived from recombinant DNA material and capable of expressing rennin, pre-prorennin and prorennin. The rennin, pre-prorennin and prorennin are derived from cells which are themselves or have had parents thereof treated by recombinant DNA methods to allow production of the desired enzymatic proteins during growth in culture.

34 Claims, 2 Drawing Sheets

OTHER PUBLICATIONS

Harris, T. J. R., et al., "Molecular cloning and nucleotide sequence of cDNA coding for calf preprochymosin," Nuc. Acids Res. 10:2177–2187 (1982).

MacDonald, et al., "Structure of a family of rat amylase genes," Nature 287:117–122 (1980).

Ehring, et al., "In vitro and in vivo products of *E. coli* lactose permease gene are identical," Nature 283:537–540.

Williamson, et al., "Isolation of the structural gene for alcohol dehydrogenase by genetic complementation in yeast," Nature 283:214–216 (1980).

Nishimori, et al., "Cloning of the Structural Gene of Prorennin," Abs of AM of the Japan Ag. Chem. Society, 1980, p. 408.

Nishimori, et al., "Cloning of Prorenin Structural Genes," Abs. of AM of Japan Ag. Chem. Society 1981, cf. PTO–1019.

Beppu, et al., "Cloning of cDNA of calf prorennin in *E. coli*," Proceedings IV Int. Fermentation, p. 179, F–21–5(L) (1980).

Hitzeman, et al., "Expression of a human gene for interferon in yeast," Nature 293:717–722 (1981).

Houghton, et al., "The amino–terminal sequence of human fibroblast interferon as deduced from reverse transcripts obtained using synthetic oligonucleotide primers," Nucl. Acids Res. 8:1913–1931 (1980).

Martin, et al., "Kinetic Studies on the Action of *Mucor pusillus, Mucor miehi* Acid Proteases and Chymosins A and B on a Synthetic Chromophoric Hexapeptide," Biophys. Acta. 612:410–420 (1980).

Collin, et al., "Immunological identification of milk clotting enzymes," J. Dairy Research 49:221–230 (1982).

Martin, et al., "Qualitative and quantitative analysis of commercial calf and bovine rennets," Neth. Milk Dairy J., 35:370–373 (1981).

Prager, "Differentiation of Rennet from Other Milk–Clotting Enzymes by Polyacrylamide Gel Electrophoresis," J. AOAC 60:1372–1374 (1977).

O'Leary et al., "A method for the quantitative analysis of the enzyme complement of commercial rennets" J. Dairy Research 41:381–387 (1974).

Molinari, et al., "Isoelectric focusing of milk–clotting enzymes," J. Dairy Research 44:69–72 (1977).

Matheson, et al., "The Immunochemical Determination of Chymosin Activity in Cheese," N. Z. J. Dairy Sci. and Tech. 15:33–41 (1981).

Vigyazo, et al., "Comparative Investigations into the Action of Chymosin and a Microbial Milk–Clotting Enzyme Preparation on Some Milk Proteins—I. Decomposition of $\alpha_s$ Casein," Acta Alimentaria 9:383–390 (1980).

Kay, et al., Neth. Milk Dairy J. 35:281–286 (1981).

Ernstrom, et al., Fund. of Dairy Chem. pp. 103–124, 604, 606–608, 662–718 and 753–771.

Foltman, et al., "The Primary Structure of Calf Chymosin," J. Biol. Chem. 254:8447–8456 (1979).

Nishimori, et al., "Expression of cloned calf prochymosin gene sequence in *Escherichia coli*," Gene 19:337–344 (1982).

Emtage, et al., "Synthesis of calf prochymosin (prorennin) in *Escherichia coli*," Proc. Natl. Acad. Sci. 80:3671 (1983).

Mellor, et al., "Efficient synthesis of enzymatically active calf chymosin in *Saccharomyces cerevisiae*," Gene 24:1 (1983).

Büchel, et al., "Sequence of the lactose permease gene," Nature 283: 541–545 (1980).

Guarente, et al., "A Technique for Expressing Eukaryotic Genes in Bacteria", Science 209:1428–1430 (1980).

RECOMBINANT DNA MEANS AND METHOD FOR PRODUCING RENNIN, PRORENIN AND PRE-PRORENNIN

RELATED APPLICATION

This application is a continuation of application Ser. No. 06/640,514 filed Aug. 13, 1984, now abandoned which is a continuation of Ser. No. 325,481 filed Dec. 1, 1981, now U.S. Pat. No. 4,666,847 issued May 19, 1987 which is a continuation-in-part of Ser. No. 225,717 filed Jan. 16, 1981 (now abandoned).

BACKGROUND OF THE INVENTION

The enzymatic protein rennin has long been know as useful for coagulating milk casein in cheese making. It is also used in connection with cheese-ripening because of its specific proteolytic activity. In the past, it has been obtained from rennet in commercial manufacture. Milk-fed calves can be butchered and the fourth stomach removed freed of its food content. A complicated method is then used wherein the stomachs are dried, salted, and frozen. At factory points, the stomachs are washed, freed of salt and treated to remove surface fat. They are then stretched on racks and dried. The dried stomachs are often cold stored then ground and placed into large vats with a brine solution circulated through the skins until extraction of rennin is completed. The above procedure for preparing rennin is costly, and presents many difficulties in producing large amounts needed for commercial use in various applications throughout the world.

SUMMARY OF THE INVENTION

It is an object of this invention to obtain living cells which are capable of producing rennin in culture for volume production.

It is a still further object of this invention to obtain living cells which are capable of producing prorennin in culture for volume production.

It is a still further object of this invention to obtain living cells which are capable of producing pre-prorennin in culture for volume production.

It is another object of this invention to provide rennin, prorennin, or pre-prorennin derived from living cells in accordance with the preceding objects which living cells contain genetic material derived from recombinant DNA material.

It is still another object of this invention to provide specialized rennin genes, pre-prorennin genes and prorennin genes.

It is still another object of this invention to provide methods of producing rennin, prorennin or pre-prorennin using recombinant DNA techniques.

It is still another object of this invention to provide signal sequences for use in transporting selected amino acid sequences such as selected enzymes or protein material to periplasmic space, other cellular areas or extracellularly with the appropriate host.

It is still another object of this invention to provide particular modified cells for use in production of polypeptides displaying rennin or milk clotting activity.

According to this invention, living cells contain genetic material derived from recombinant DNA material and are capable of expressing rennin or pre-prorennin or prorennin. The invention also comprises the rennin, prorennin and pre-prorennin and the genes therefor, derived from living cells.

According to a method of this invention, expression of pre-prorennin in a host cell is obtained by generating a DNA sequence that codes for pre-prorennin. That sequence has attached to it a transcriptional promoter and a ribosomal binding sit at the 5' end and the distance between the beginning of the DNA that codes for pre-prorennin and the segment of DNA carrying the promoter and binding site is varied. The DNA is then transformed into host cells. The host cells are cloned and those that have high levels of expression of pre-prorennin are selected.

In a method of obtaining expression of prorennin or rennin in host cells, a DNA sequence that codes for pre-prorennin and having a 5' end is selected. A portion is removed from the 5' end which portion codes for the prorennin or rennin precursor polypeptide. The remainder bearing the prorennin or rennin coding sequence is ligated onto a synthetic piece of DNA carrying a translational initiation codon at the 3' end of the piece. One then proceeds as before by attaching a transcriptional promoter and ribosomal binding site to the sequence and varying the distance between the beginning of the DNA that codes for prorennin or rennin and the segment of DNA carrying the promoter and ribosome binding site. This material is transformed into host cells, cloning is carried out and selection of the cells that express prorennin or rennin as desired and selected above is carried out.

*Escherichia coli* prepared by a process described herein are exemplified by a culture deposited in the American Type Culture Collection of 12301 Park Warren Drive, Rockville, Md. 20852 and identified as Accession No. 31929 which is strain CGE24 a derivative of *E. coli* strain BNN45.

Yeast microorganisms prepared by the process described herein are exemplified by cultures deposited in the American Type Culture Collection of 12301 Park Warren Drive, Rockville, Md. 20852 and identified as Accession No. 20623 which is strain CGY116 a derivative of *Saccharomyces cerevisiae* strain CGY80.

Preferably in the methods of this invention pre-prorennin, prorennin and rennin can each be obtained by isolation of pre-prorennin DNA material. The pre-prorennin is a precursor of prorennin and is not described in the literature. By removing portions of the pre-prorennin DNA, one could obtain genetic material which will code for prorennin or for rennin.

Pre-prorennin, prorennin or rennin genes in accordance with this invention comprise any nucleotide sequences coding for the amino acid sequence of pre-prorennin, prorennin or rennin respectively and exclude any intervening nucleotide sequences present in the genomic DNA encoding pre-prorennin, prorennin or rennin respectively. These three genes are also provided attached to vectors which replicate in suitable host cells.

The cells are preferably *E. coli* which are capable of expressing recombinant DNA material to produce the desired enzymatic protein. Yeast and other cells can also be used. These cells are selected to be capable of producing large quantities of the enzymatic protein under reasonable commercial culture conditions.

The enzyme rennin (EC 3.4.23.4), which is referred to in this application is also known as chymosin. It is the major proteolytic protein found in the stomach of the pre-ruminant calf and is responsible for clotting milk. Rennin is used commercially for the production of cheese. Prorennin is a precursor form of rennin having 42 additional amino acids at the amino terminal end as described by B. Foltmann et al, *Proc. Nat. Acad. Sci. USA* 74 2321–2324 (1977). Pre-prorennin, first described in this application, is a precursor form of prorennin and has a number of additional amino acids (preferably 16 amino acids) on the amino terminal end of the prorennin molecule. These additional amino acids are probably important for secretion of the enzyme from the stomach cells. B. Foltmann and others have shown that purified rennin is a mixture of two forms, A and B, (B. Foltmann et al, *Proc. Nat. Acad. Sci. USA* 74 2321–2324 (1977) and *J. Biol. Chem.* 254 8447–8456 (1979). Both forms are active, and sequencing data indicates that probably the only difference is an aspartate residue at position #290 in rennin A and a glycine residue at that position in rennin B. The rennin produced in the examples of this invention is rennin A; however, the same procedures and/or simple conversions can enable production of rennin B. Similarly the pre and pro forms may occur in an A or B form.

For the purpose of this application, the prorennin gene is defined as any sequence of nucleotides which codes for the prorennin molecule, the amino acid sequence of which is described in the literature (B. Foltmann, V. B. Pedersen, H. Jacobsen, D. Kauffman, and G. Wybrandt, *Pro. Nat. Acad. Sci. USA* 74, 2321–2324 (1977).

The pre-prorennin gene includes the sequence of nucleotides coding for prorennin, but also includes 48 additional nucleotides of the 5' end which code for the amino-terminal precursor polypeptide found on the pre-prorennin enzyme.

The rennin gene is defined as any sequence of nucleotides which code for the prorennin molecule excluding the first 126 nucleotides which encode the proenzyme portion of prorennin.

The living cells are prepared in the first instance by using a plurality of known DNA technologies starting with materials obtained from the fourth stomach of a calf.

It is a feature of this invention that the rennin, pre-prorennin and prorennin obtained can be used in cheese-making to clot milk to obtain cheese and perhaps in other commercial applications to clot milk to obtain cheese. Large volumes can be produced by culture techniques. Thus large amounts of materials are capable of being produced at reasonable production rates and costs. The genetic recombinant DNA material is substantially identical to the rennin portion of the calf pre-prorennin gene which rennin is to be produced, substantially identical to the calf pre-prorennin gene when pre-prorennin is to be produced and substantially identical to the prorennin portion of the calf pre-prorennin gene when prorennin is to be produced. The differences in the recombinant DNA material relate mainly to the molecules being devoid of introns that may exist in the calf gene.

Any species of bacteria which is considered safe for recombinant DNA work can be used, including, for example, *Escherichia coli,* various species of Bacillus such as *Bacillus subtilis,* various Lactobacillus species, and various Micrococcus species such as *Micrococcus fragilis.* Other cells such as fungi, yeast or mammalian cells can also be used as host cells. In each case, the genetic information of the cells which result, contain new genetic material derived from recombinant DNA material. This material is often contained in the form of a plasmid which is capable of replicating in the host cell and has inserted therein genetic material from a donor cell at some initial stage. Once the recombinant DNA molecule is formed and inserted into the host cell, that host cell grows and reproduces by essentially normal means. Production of the enzymatic protein which the recombinant DNA material encodes, which can be rennin, pre-prorennin or prorennin, occurs in accordance with this invention.

DESCRIPTION OF PREFERRED EMBODIMENTS

Figure 1:
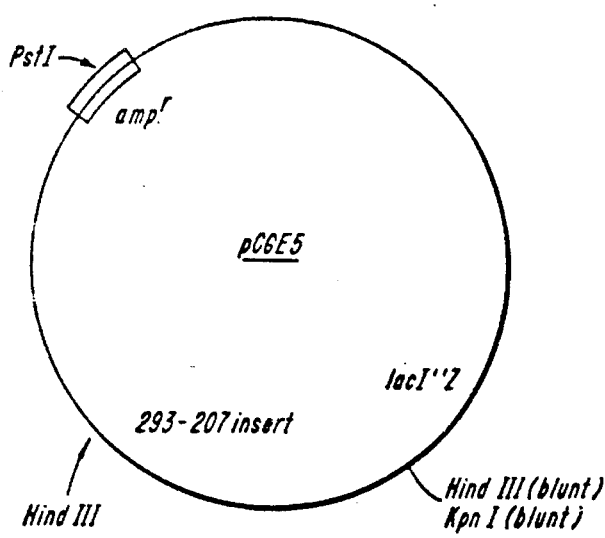
FIG. 1 is a schematic representation of plasmid pCGE5.

The host cells into which the desired recombinant DNA material is introduced are preferably derivatives of *E. coli* K-12. Useful derivatives are as follows:

HB101, H. W. Boyer & D. Roulland-Dussoix (1969) *J. Mol. Biol.* 41 459–472,

C600, M. Mandel & A. Higa *J. Mol. Biol.* 53 159–162 (1970), and derivatives of C600 such as:

MV1 and MV12, V. Hershfield, H. W. Boyer, C. Yanofsky, M. A. Lovett & D. R. Helinski (1974) *Proc. Natl. Acad. Sci. USA* 71 3455–3459, LE392, S. M. Tilghman, D. C. Tiemeier, F. Polsky, M. H. Edgell, J. G. Seidman, A. Leder, L. W. Enquist, B. Norman & P. Leder (1977) *Proc.Natl Acad.Sci.USA* 74 4406–4410, JM101, J. Messing (1979) Recombinant DNA Technical Bulletin 2 43–48, W3110 and derivatives, K. L. Korn & C. Yanofsky (1976) *J.Mol.Biol.* 103 395–409.

The cells can be grown by conventional culturing techniques. For example, culture media for the *E. coli* can be:

Rich media:

| LB | per liter | |
|---|---|---|
| | 10 g Bacto tryptone (Difco Laboratories, Detroit) | |
| | 5 g Bacto yeast extract (Difco Laboratories, Detroit) | |
| | 10 g Nacl | |
| | 2 g glucose | |
| TY | per liter | |
| | 10 g Bacto tryptone (Difco Laboratories, Detroit) | |
| | 1 g Bacto yeast (Difco Laboratories, Detroit) | |
| | 8 g Nacl | |
| | 1 g glucose | |

Minimal media:

| | M9 | per liter | |
|---|---|---|---|
| | | $NaHPO_4$ | 6 g |
| | | $KH_2PO_4$ | 3 g |
| | | NaCl | 0.5 g |
| | | $NH_4Cl$ | 1 g |
| | | $CaCl_2$ | 11 mg |
| | | $MgSO_4 7H_2O$ | 0.2 g |
| | | B1 (thiamine HCl) | 5 mg |

-continued

Minimal media:

amino acids as required by the strain
(40 mg each)
glucose        2 g

The cultures can be grown in suspension, plated on agar medium, or other standard tissue and cell culture techniques can be used.

The culture media used can be any of the standard culture media for growing the particular cells. For example, TY medium with the cells initially seeded at a level of 1% to 4% where *E. coli* LE392 (*E. coli* C600 $r_k^- m_k^+$ SupE, SupF, gal⁻) or BNN45 (*E. coli* hsdR⁻, hsdM⁺, SupE, SupF, B1⁻ met⁻) (*Advanced Bacterial Genetics,* R. W. Davis, D. Botstein, J. R. Roth, Cold Spring Harbor Laboratory [1980] p.7) is preferred.

In standard techniques, the *E. coli* are grown to a density of from 10 to $30 \times 10^{12}$ cells/liter and the desired enzymatic protein is produced.

Various media known for growing cells can be used and form no part of the present invention. Similarly a variety of growing methods, techniques and conditions can be used. For example, while the cells are preferably grown at temperatures of from 30 degrees C. to 40 degrees C., temperature outside of this range can be used.

The starting point for obtaining the cells of the present invention is the use of recombinant DNA techniques known in the art to obtain the genetic material desired and to insert it into the host cell after which the host cell is cloned.

Preferably, the rennin gene, pre-prorennin gene of prorennin gene which one wishes to ultimately clone in an organism is isolated in a first step by obtaining messenger RNA of the pre-prorennin gene from a tissue source. In the case of the calf, this is obtained by isolation from the fourth calf stomach. The messenger RNA can be isolated as by the method of Deeley et al (R. G. Deeley, J. I. Gordon, A. T. H. Burns, K. P. Mullinix, M. Bina-Stein, R. F. Goldberger *J. Biol. Chem.* 252 8310–8319 [1977]) and poly A-enriched RNA can be obtained by chromatography over oligo (dT) cellulose by the method of R. C. Desrosiers, K. H. Friderici, & F. M. Rottman *Biochemistry* 14 4367–4374 (1975).

The messenger RNA is then converted to double-stranded DNA by conventional means. First, the complimentary copy of the DNA is made from the messenger RNA by conventional recombinant DNA means as by the use of AMV reverse transcriptase. For example, the methods of A. Efstratiadis, F. C. Kafatos, A. M. Maxam and T. Maniatis, *Cell* 7 279–288 (1976), R. Higuchi, G. V. Paddock, R. Wall and W. Salser, *Proc. Nat. Acad. Sci. USA* 73, 3146–3150 (1976), D. L. Kacian and J. C. Myers, *Proc. Nat. Acad. Sci. USA* 73, 2191–2195 (1976), M. P. Wickens, G. N. Buell and R. T. Schimke, *J. Biol. Chem.* 253, 2483–2495 (1978), G. M. Wahl, R. A. Padgett and G. R. Stack, *J. Biol. Chem.*, 254, 8679–8689 (1979) can be used to obtain the copy DNA (cDNA). The RNA portion can be disposed of by breaking the strands as known in the art using any of the above methods or by heat denaturing according to the method of Wickens et al (1978).

Next, enzymes such as *E. coli* DNA polymerase I or AMV reverse transcriptase can be used to turn the cDNA into double-stranded DNA using the methods of the publications above and J. I. Gordon, A. T. H. Burns, J. L. Christmann & R. G. Deeley, *J. Biol. Chem.* 253, 8629–8639 (1978).

Thirdly, synthetic linkers can be attached to both ends of the double-stranded DNA as for example by the use of Hind III or Eco R1 synthetic oligonucleotide linkers using conventional methods such as described in R. H. Scheller, T. L. Thomas, A. S. Lee, W. H. Klein, W. D. Niles, R. J. Britten and E. H. Davidson, *Science* 196, 197–200 (1977), T. H. Fraser and B. J. Bruce, *Proc. Natl. Acad. Sci. USA* 75 5936–5940 (1978), A. Ullrich, J. Shine, J. Chirgwin, R. Pictet, E. Tischer, W. J. Rutter & H. M. Goodman, *Science* 196, 1313–1319 (1977), J. Sine, P. H. Seeburg, J. A. Martial, J. D. Baxter & H. M. Goodman, *Nature* 270, 494–499 (1977), or P. H. Seeburg, J. Shine, J. A. Martial, J. D. Baxter & H. M. Goodman, *Nature* 270, 486–494 (1977).

In a fourth step, the DNA molecule is integrated into the chromosome or attached to a vector which can be a plasmid, virus or cosmid as known in the art. Such vectors include:

pBR322 (F. Bolivar, R. L. Rodriguez, P. J. Greene, M. C. Betlach, H. L. Heyneker, H. W. Boyer, J. H. Crosa, S. Falkow, 1977 *Gene* 2 95–119) pMB9 (R. L. Rodriguez, F. Bolivara, H. M. Goodman, H. W. Boyer, M. C. Betlach in "Molecular Mechanisms in the Control of Gene Expression" [D. P. Nierlich, W. J. Rutter, C. F. Fox, Eds.] 471 Academic Press New York 1976) pSC101 (S. N. Cohen, A. C. Y. Chang, H. W. Boyer, R. B. Helling 1973 *Proc. Nat. Acad. Sci. USA* 70 3240)

λgtWES (D. Tiemeier, L. Enquist, P. Leder *Nature* 263 526–527) (1976)

λcharon phages (F. R. Blattner, et al *Science* 196 161–169) (1977)

f1 R229 (J. D. Boeke *Molec. Gen. Genetics* 181, 288–291) (1981)

pJC75-58 (J. Collins *Methods in Enzymology* 68 309–326) (1979)

This step is again carried out outside of the final host cell. Useful techniques for this procedure are described in the references above in connection with the linkers as well as in the following publications: V. Hershfield, H. W. Boyer, C. Yanofsky, M. A. Lovett & P. R. Helinski, *Proc. Natl. Acad. Sci. USA* 71, 3455–3459 (1974), N. E. Murray & K. Murray, *Nature* 251, 476–482 (1974), F. R. Blattner et al, *Science* 196, 161–169 (1977).

In a fifth step, the recombinant DNA molecule can be introduced into the cytoplasm of the host cell line using conventional procedures such as described in M. Mandel & A. Higa (1970) *J. Mol. Biol.* 53 159–162, P. C. Wensink, D. J. Finnegan, J. E. Donelson & D. S. Hogness, *Cell* 3, 315–325 (1974), S. N. Cohen, A. C. Y. Chang and L. Hsu, *Proc. Natl. Acad. Sci. USA* 69, 2110–2114 (1972), H. M. Goodman, and R. J. MacDonald, *Methods in Enzymology* 68, 75–90 (1979), E. M. Lederberg and S. N. Cohen, *J. Bact.* 119, 1072–1074 (1974).

Recognition of the correct clone may be accomplished by the method of hybridization selection or by probing with synthetic oligonucleotides, (T. Taniguchi, Y. Fujii, Kuriyama and M. Muramatsu, *Proc. Natl. Acad. Sci. USA* 77, 4003–4006 (1980), R. P. Ricciardi, J. S. Miller & B. E. Roberts, *Proc. Natl. Acad. Sci. USA* 76, 4927–4931 (1979), D. L. Montgomery, B. D. Hall, S. Gillam and M. Smith, *Cell* 14, 673–680 [1978]).

The newly modified host cell is then cloned and expression of the material desired obtained. For example, the technique of Guarente et al using the lactose operon promoter, (1980) (L. Guarente, G. Lauer, T. M. Roberts & M. Ptashne, *Cell* 20, 543–553 [1980], L. Guarente, T. M. Roberts & M. Ptashne, *Science* 209, 1428–1430 [1980]) allows one to obtain and optimize expression of foreign DNA. Other promoters can be used to obtain expression as known in the art so long as that promoter is active in the desired bacterial, yeast or other host cell. Such promoters include the *E. coli* tryptophan operon, or beta-lactamase promoters, and *S. cerevisiae*, uracil 3 or invertase promoters.

In a specific example of this invention, recombinant *E. coli* strains can be obtained which produce pre-prorennin A, prorennin A or rennin A as follows:

1. Isolation of the RNA

Stomach tissue from milk-fed calves was obtained fresh from a local slaughterhouse; the mucosa of the fourth stomach was dissected away from the stomach wall and frozen in dry ice. Twenty-one grams of the mucosal tissue was disrupted by means of a blender into 200 ml of cold buffer (10 degrees C.) consisting of 50 mM Tris.HCl, pH 7.5, 8M guanidine HCl, and 1 mM dithiothreitol. Insoluble material was removed by centrifugation in a Sorvall SA-600 rotor at 10,000 rpm for 12 minutes. To the 200 ml of supernatant from the spin was added 100 ml of ice cold absolute ethanol. After 1.5 hours at −20 degrees C., the precipitate was pelleted by a centrifugation at 3000 rpm for 30 minutes at −10 degrees C. The pellet was dissolved in 40 ml of ice cold buffer (EGAD) consisting of 20 mM EDTA, pH7, 20 mM NaOAc, pH7, 8M guanidine.HCl, and 1 mM dithiothreitol. Twenty milliliters of cold absolute ethanol was added and the solution placed at −20 degrees C. for 45 minutes. The precipitate was pelleted by centrifugation at 3000 rpm for 20 minutes at −10 degrees C. The pellet was redissolved in 40 ml cold EGAD buffer and the precipitation with 20 ml cold ethanol, centrifugation and redissolving the pellet in EGAD buffer was repeated two additional times. Finally, the pellet was dissolved in 16 ml of 20 mM EDTA, pH 7 and extracted three times with chloroform;isobutanol (4:1). Next, two volumes of 4.5M NaOAc pH5.2 was added to the aqueous layer and the solution was placed at −20 degrees C. overnight. The RNA precipitate was collected by centrifugation at 10,000 rpm for 25 minutes at −10 degrees C., and was dissolved in 30 ml water. The yield was 45 mg RNA. The RNA was precipitated by addition of 1 ml of 2M NaOAc pH5 and 75 ml absolute ethanol, followed by incubation at −20 degrees C. overnight. The RNA was pelleted by centrifugation (10,000 rpm, 10 minutes −10 degrees C.) and redissolved in 20 ml water, heated to 60 degrees C. for 10 minutes, chilled rapidly on ice and diluted with 21 ml of 2x concentrated binding buffer (20 mM Tris.HCl pH7.5, 2 mM EDTA pH7, 0.4% SDS and 0.24M NaCl). The RNA was applied to a 4 ml oligo-dT-cellulose column, the column was washed with 45 ml of 1x concentrated binding buffer, and then the poly A-containing RNA was eluted by washing the column with binding buffer containing no NaCl. About 1 mg of poly A-containing RNA was obtained. A portion of the poly A-containing RNA was translated in vitro in a rabbit reticulocyte lysate system (H. R. B. Pelham and R. J. Jackson [1976] *Eur J. Biochem.* 67 247–256). The protein products were analyzed on a 10% polyacrylamide gel. A single major protein band was observed which was precipitated with rennin antiserum showing that rennin mRNA is present in the poly A-containing RNA.

2. Preparation of double-stranded copy DNA (cDNA)

About 8.7 µg of cDNA was synthesized from 20 µg of the calf stomach poly A-containing RNA by incubation for one hour at 42 degrees C. in 50 mM Tris HCl pH8.3, 100 mM KCl, 8 mM MgCl$_2$, 0.4 mM dithiothreitol, 1 mM each deoxynucleside triphosphate, 20 µg/ml oligo(-dT)$_{12-18}$ containing 100 units reverse transcriptase and 1 Ci/mmole $\alpha^{32}$P-dCTP. After heating the reaction mixture at 100 degrees C. for 3 minutes, chilling on ice for 3 minutes and removing the precipitated protein by centrifugation, to half the supernatant material was added Hepes.KCH pH6.9 to 100 mM, MgCl$_2$ to 5 mM, dithiothreitol to 0.5 mM, deoxynucleoside triphosphates to 0.125 mM. Incubation of this mixture with 300 units of *E. coli* DNA polymerase I for 2 hours at 16° C. produced 8.6 µg of double-stranded cDNA. The DNA was phenol extracted and separated from unincorporated triphosphates by chromatography on Sephadex G-100 (12 ml column, 0.7 cm×30 cm, eluted with 20 mM Tris.HCl pH 7.5, 0.5 mM EDTA) and was ethanol precipitated overnight at −20 degrees C. by addition of ⅒volume 2M NaOAc pH5, and 2.5 volumes cold ethanol. The double-stranded cDNA (4.6 µg) was then treated with 1000 units of S1 nuclease at 37 degrees C. for 1 hour in Buffer S (0.3M NaCl, 30 mM NaOAc, pH4.6, 3 mM ZnSO$_4$). The reaction was terminated by addition of EDTA to 10 mM, and Tris.HCl pH8.3 to 200 mM, and the mixture applied to a Biogel A-150 m column (0.7 cm×33 cm) equilibrated and eluted with 10 mM Tris.HCl pH7.5, 1 mM EDTA and 250 mM NaCl. The peak fractions (0.5 ml each) of large molecular weight DNA were pooled and ethanol precipitated addition of ⅒ volume 2M NaOAC pH5 and 2.5 volumes cold absolute ethanol.

3. Addition of Hind III Linkers

S1-treated double-stranded cDNA (1.7 µg) was incubated in Buffer T (25 mM Tris.HCl pH8, 6.6 mM MgCl$_2$, 0.5 mM EDTA, 5 mM 2-mercaptoethanol and 0.5 mM of each deoxynucleoside triphosphate) with 2 units of T$_4$ DNA polymerase at room temperature for 30 minutes. The material was phenol extracted and ether extracted and ethanol precipitated by addition of ⅒ volume 2M NaOAc pH5 and 2.5 volumes ethanol. This blunt-ended double-stranded cDNA was next incubated in 66 mM Tris.HCl pH7.6, 6.6 mM MgCl$_2$, 5 mM 2- mercaptoethanol, 0.5 mM ATP, with 300 pmoles of $^{32}$P-labelled Hind III synthetic linker (100× excess over cDNA ends) and 9 blunt-end units of T$_4$ DNA ligase at 12 degrees overnight.

The reaction was adjusted to 10 mM EDTA pH8 and fractionated on a Biogel A-150 m column (0.7 cm×20 cm). Fractions (0.25 ml each) containing high molecular weight DNA were pooled and ethanol precipitated. This material was treated with Hind III restriction endonuclease (9 units) in 5.6 mM Tris.HCl pH7.6, 5.6 mM MgCl$_2$ at 37 degrees C. for 45 minutes, then phenol extracted, ether extracted and ethanol precipitated by the addition of ⅒ volume 1M NaOAc pH5 and 2.5 volume, absolute ethanol. This double-stranded cDNA with Hind III cohesive termini was then ligated to f1 phage CGF4 double-stranded DNA which had been cut open with Hind III restriction endonuclease and treated twice with calf intestinal phosphatase by the method of H. Goodman and R. J. MacDonald (H. M. Goodman and R. J. MacDonald [1979] *Methods in Enzymology* 68, 75–91) to remove the terminal phosphates (Note: In order to produce phage CGF4, f1 phage R229 (J. D. Boecke [1981] *Mole. Gen. Genet.* 181, 288–291) was cut with EcoRI endonuclease, rendered blunt-ended with T4 DNA polymerase and ligated with Hind III synthetic oligonucleotide linkers from Collaborative Research, Inc. of Waltham, Mass.). The ligation reaction contained 66 mM Tris.HCl pH7.6, 6.6 mM MgCl$_2$, 5 mM 2-mercapto-ethanol, 0.3 µg double-stranded cDNA, 0.2 µg CGF4 DNA, 0.5 mM ATP and 300 cohesive-end units of T$_4$ DNA ligase. Ligation was for 29 hours at 16 degrees C.

4. Transfection of *E. coli* BNN45 with recombinant-CGF4 DNA

*E. coli* strain CGE6 (BNN45; hsdR⁻, hsdM⁺, sup E, sup F, B1⁻, met⁻) was grown in tryptone broth at 37 degrees C. with shaking and harvested at $OD_{700}=0.5$ by centrifugation at 7000 rpm for 10 minutes at 4 degrees C. The cells were resuspended in ice cold 50 mM $CaCl_2$ (one-half the original culture volume) and allowed to sit at 0 degrees C. for 30 minutes. The suspension was then centrifuged at 7000 rpm for 10 minutes at 4 degrees C. and resuspended in ¹/₂₀ the original culture volume ice cold 50 mM $CaCl_2$. After standing at 0 degrees C. for 60 minutes the cells were used for transfection. One-half microliter of the 20 μl ligation reaction was added to each of 8 tubes containing 50 μl sterile 50 mM Tris.HCl pH7.6. One-tenth milliliter of the $CaCl_2$-treated cells was added to each tube and the mixtures sat on ice for 30 minutes. After warming to 37° C. for two minutes, 0.2 ml of a CGE5 (JM101:J. Messing [1979], F'tra D36 pro AB lac IZ∇M15 in a ∇ (lac pro) SupEthi⁻ background) overnight culture and 3 ml of 0.7% soft agar were added, and the mixture poured onto eight tryptone agar plates. Incubation at 37 degrees C. overnight produced about 250 plaques per plate.

5. Identification of a Recombinant CGF4 carrying the rennin coding sequence

The plaques were transferred to nitrocellulose and probed as described by Benton & Davis (W. D. Benton and R. W. Davis [1977] *Science* 196, 180–182) using ³²P-labelled cDNA made from the calf-stomach poly A-containing RNA using $\alpha^{32}$p-dCTP and reverse transcriptase (T. P. St. John and R. W. Davis [1979] *Cell* 16 443–452). About 80 recombinant phage which hybridize intensely to the labelled cDNA were picked from the plates and stored in TY medium at 4 degrees C. Samples of the intact phage were amplified by growth overnight on CGE5 cells, harvested by centrifugation, and subjected to electrophoresis in a 2% agarose gel containing 0.37M Tris.glycine pH9.5 and stained with ethidium bromide after treatment in 0.2N NaCH for one hour and neutralization in 0.5M Tris HCl pH7.4. The migration is inversely proportional to the log of the size of the phage DNA and allowed selection of eight phage carrying inserted DNA of size 1000 to 2000 base pairs. Double-stranded RFI DNA was prepared from these eight phages by the method of Moses et al (P. B. Moses, J. D. Boeke, K. Horiuchi & N. D. Zinder [1980] *Virology* 104, 267). This DNA was cut with Hind III and the resulting fragments analyzed on an agarose gel to confirm that the insert was in the Hind III site and of the anticipated size. Finally, the DNA from four of the recombinant phages (approximately 5–10 μg from each) and DNA from the vector CGF4 was cut with Hind III and the fragments, after denaturation by boiling for 45 seconds and freezing in dry ice/ethanol, were bound to nitrocellulose by spotting the DNA in water onto small pieces of nitrocellulose pretreated with 20x SSC and dried. After baking in vacuo at 75 degrees C. for 1.5 hours, the DNA bound to nitrocellulose was carried through the hybrid selection procedure as described by Miller et al (J. S. Miller, R. P. Ricciardi, B. E. Roberts, B. M. Paterson & M. B. Mathews [1980] *J. Mol. Biol.* 142, 455–488) using 2 μg poly A-enriched calf stomach RNA for each hybridization. The eluted RNA was then translated in a reticulocyte lysate system labelling with ³⁵S-methionine by the method of Pelham and Jackson (H. R. B. Pelham & R. J. Jackson [1976] *Eur. J. Biochem.* 67, 247–256) and the resulting protein products analyzed on a 10% polycrylamide gel containing 0.1% SDS according to Laemmli (U. Laemmli [1970] *Nature* 227, 680–685). The results of the gel analysis indicated that all four of the phage DNAs tested did hybridize to the rennin mRNA since all four selected an RNA species which, upon translation in a rabbit reticulocyte lysate, yields a protein product identical to pre-prorennin in size and immunological criteria. Two of the four, 293–207 which has an insert of about 1400 base pairs (bp) and 293-118/37 which has an insert of about 1250 bp, were chosen for further study. The DNA inserts were sequenced by the method of Maxam and Gilbert (A. M. Maxam and W. Gilbert [1980] *Methods in Enzymology* 68, 499–560). From nucleotide 205 to 1350 is the DNA sequence for the pre-prorennin A gene (see Table 1). The nucleotide sequences 1–204 and 1351 to 1460 are attached to the pre-prorennin but can be removed if desired and are not essential to use of the gene in expression. Useful portions of the DNA material of Table 1 can be separated and used by known techniques.

TABLE 1

```
                                                30                              60                              90
AAG CTT GGG CGA GCG AGG GGT AGG CCA GGA TCC CGT CGA ATT CGG CAT AGC AGA CGT CCC CGG GCT CCT GGG TGC TCA GGC 120                             150                             180
CTA CTG TCT GCT GGA TGT CCA CAA TGT TGG AGA CAG TGA CGG TGT CAT AGC CCA GGA TGC CCT GCA GTC CTG TCC CGT AGT GGA TAG
LEU LEU SER ALA GLY CYS PRO GLN CYS TRP ARG GLN                                                 MET ARG CYS 210                             240                             270
ACA GCG TCT GGA CCC AGA TCC AAG ATG AGG AAG TCT CTG GCT GTG GAG CTT CTG GTC GTC CTG GCT CTC TCC CAG GCT GAG ATC ACC AGG ATC
                                MET ARG LYS SER LEU ALA VAL GLU LEU LEU VAL VAL LEU ALA LEU SER GLN ALA GLU ILE THR ARG ILE 300                             330                             360
CCT CTG TAC AAA GGC AAG TCT CTG AGG CTG GTG CAT GAG CTT CTG GGG CAT CTG GAG GAC TTC CTG TAC CAG AGC ATC AGC
PRO LEU TYR LYS GLY LYS SER LEU ARG LEU VAL HIS GLU LEU LEU GLY HIS LEU GLU ASP PHE LEU TYR GLN SER ILE SER 390                             420                             450
AGC TAC CTC TCC GGC GAG TTC TCC GGG GAG GTG GCC AGC GTG GCC CTG AGT GAT CAG TTT GGG AAG ATC TAC CTC GGG ACC
SER TYR LEU SER GLY GLU PHE SER GLY GLU VAL ALA SER VAL ALA LEU SER ASP GLN PHE GLY LYS ILE TYR LEU GLY THR 480                             510                             540
CCG CCC CAG GAG GTG CTG TTT GAC TAT GCG CAG TTC CAG ACC GTG CTC TCT CAG GGC CTG AGT TTC TGC AAG AGC AAT GCC AGC AGC AAC AAC
PRO PRO GLN GLU VAL LEU PHE ASP TYR ALA GLN PHE GLN THR VAL LEU SER GLN GLY LEU SER TYR CYS LYS SER ASN ALA CYS LYS ASN ASN 570                             600                             630
CAC CAG TTC GAC ACC ACC GTC ACT GTC AGA AAG CCG TAC CCG AGC CAG GAG GAC ATC ATC CAC TAC CTG CAG AGC ATG AGC AGC AGG CCC GAC GTC TTC
HIS GLN PHE ASP THR THR VAL THR VAL ARG LYS PRO TYR PRO SER GLN GLU ASP ILE ILE HIS TYR LEU GLN SER MET GLN ARG GLY ASP VAL PHE 660                             690                             720
ATC CTG GGC TAT GAA TTC GAC GTC ACC GTC ACC GAT TTC TTC AAC ATT GTG GAC ATC ATC CCC TCG CCC TAC ATA CCC ATG CTG CTC ACG CTG GGG GCC ATC AGC GTG TTT
ILE LEU GLY TYR GLU PHE ASP LEU LEU VAL THR GLY LEU ILE LEU SER ALA LEU TYR ASN ILE PRO LEU TYR ILE LEU ALA THR TYR LEU GLY LEU TYR ASN MET ASN 750                             780                             810
ACC TAT GCC GAA TTC GAC GAG TTC GAC AGG CTG GTA GGC TTC ATG GAC AGG CAG TGG CAG TTC TGG CAG TTC TGG CAG TTC TAC ATG GAC AGC CAG GAG TAC GGG AGT GAG GCG
THR TYR ALA GLU PHE ASP GLU PHE ASP ARG LEU VAL GLY PHE MET ASP ARG ARG GLN GLN TRP GLN ASP GLU CAG VAL PHE ASP ASN MET MET ASN 840                             870                             900
AGG CAC CTG GTC CAA GAC CTG GTT TAC ATG GAC AGC CCC GTG ACG ACG GGC ACG GGC ACC ATC ACC ATC AGC GAC AGC CCC AGT GTT GAG AGC AGG GAC GTG CTG GGG GCC ATC AGG GAC CCG TCC
ARG HIS LEU VAL GLN ASP LEU VAL TYR MET ASP SER PRO VAL ASN GLY TRP GLN TYR GLN LEU VAL ASN GLY CCC VAL PHE GLY PRO ASP ASN MET MET ASN 930                             960                             990
TAC TAC ACA GGG TCC CTG CAC TGG TGC CAG CTG GTC CCC ATC CTG GAC ACG GAC AGT GTC ACC ATC AGC GGT GTT
TYR TYR THR GLY SER LEU HIS TRP GLN TYR THR ALA LEU ALA TYR VAL PRO GLU LEU ASP SER SER VAL THR ILE SER GLY VAL VAL 1020                            1050                            1080
GTG GCC TGT GGT GGC GGC GGC TGT CAG CAG TCC CAG CAG TCC GGG CCC AGC AGC GAC ATC CTC AAC ATC CAG CAG
VAL ALA CYS GLY GLY GLY CYS GLN LEU ALA ILE ALA GLY ILE ASP LEU GLY VAL PRO SER SER ASP ILE LEU ASN ILE GLN GLN 1110                            1140                            1170
GCC ATT GGA GCC ACA CAG AAC CAG AAT GGA CAG TAC TAC GAT GAG TTT GAC ATC GAC TGC AGC TAC ATG CCC ACT GTG GTC TTT GAG ATC AAT
ALA ILE GLY ALA THR GLN ASN GLN ASN GLY GLN TYR ASP GLU PHE ASP ILE ASP CYS SER TYR MET PRO THR VAL VAL PHE GLU ILE ASN
```

TABLE 1-continued

```
                                    1200                           1230                           1260
GGC AAA ATG TAC CCA CTG ACC CCC TCC GCC TAT ACC AGC CAG GAC CAG GGC TTC TGT ACC AGT GAA AAT CAT TCC CAG
GLY LYS MET TYR PRO LEU THR PRO SER ALA TYR THR SER GLN ASP GLN GLY PHE CYS THR SER GLU ASN HIS SER GLN
                                    1290                           1320                           1350
AAA TGG ATC CTG GGG GAT GTT TTC ATC CGA GAG TAT TAC AGC TTT GAC AGG GCC AAC CTC GTG GGG CTG GCC AAA GCC ATC TGA
LYS TRP ILE LEU GLY ASP VAL PHE ILE ARG GLU TYR TYR SER PHE ASP ARG ALA ASN LEU VAL GLY LEU ALA LYS ALA ILE
                                    1380                           1410                           1440
TCA CAT CGC TGA CCA AGA ACC TCA CTG TCC CCA CAC ACA TGC ACA CAT GTA CAT GGC ACA TGT GCA CAC ACA CAG ATG
AGG TTT CCA GAC CCA AGC TT
```

This Table combines information from both 293–207 and 293-118/37: recombinant phage 293-207 carries an insert bearing the sequence shown in Table 1 from nucleotide #1 to at least nucleotide #1360 except for nucleotides 848–961 which are deleted, while phage 293–118/37 carries an insert bearing the sequence from nucleotide #229 to nucleotide #1460. As revealed by the sequencing results, initiation of rennin synthesis occurs at a methionine codon (nucleotides 205–207) and results in a pre-prorennin molecule with sixteen additional amino acids compared to purified prorennin (The prorennin B amino acid sequence was published by B. Foltmann et al. *Proc. Nat. Acad. Sci. USA* 74 2321–2324 (1977) and B. Foltmann et al *J. Biol. Chem.* 254 8447–8456 (1979); the nucleotide sequencing data of Table 1 is the first indication for the existence of pre-prorennin). Together, the two recombinant f1 phages 293-207 and 293-118/37 carry the DNA sequence for the entire pre-prorennin A molecule. The prorennin portion of the pre-prorennin A differs from prorennin B at amino acid #290 (aspartate in rennin A and glycine in rennin B as described by Foltmann et al [see above]; amino acid position numbering is that of Foltmann). An asparagine codon is shown at amino acid position #204 while Foltmann reported an aspartate at the position; however, this may be an amino acid sequencing error since the amides of aspartate and glutamate are difficult to distinguish from their acid forms, while nucleotide sequencing can readily distinguish the codons.

The cloned rennin gene represented by phage 293-118/37 was used to investigate properties of the bovine genomic copy or copies of the rennin gene. These experiments were done by hybridizing cloned rennin DNA labelled with 32P by the method of nick-translation (P. W. J. Rigby, M. Dieckmann, C. Rhodes, and P. Berg [1977] *J. Mol. Biol.* 113, 237–251) to bovine DNA cut with various restriction enzymes, separated with an agarose gel and transferred to a nitrocellulose membrane according to the method of Southern (E. M. Southern [1975] *J. Mol. Biol.* 98, 503–517). The results indicate that restriction endonuclease cleavage of the bovine DNA the enzymes such as SacI and BglI, which do not cut the cloned pre-prorennin cDNA sequences, nevertheless frequently yields more than one band of DNA which will hybridize to the rennin sequence. This suggests (a) that the genomic copy of rennin information contains additional DNA, presumably intervening sequences, which contain restriction enzyme sites not found in rennin cDNA, or (b) that more than one rennin gene exists in the genome and some restriction enzymes cut between the copies. This latter possibility was eliminated by hybridizing restriction cut bovine genomic DNA with $^{32}$P-labelled probes derived from the 5' and 3' ends of the cloned rennin cDNA. These results, using restriction endonucleases EcoRI and BamHI for example, are consistent with a single genomic copy of rennin coding information. This means that A and B forms of rennin observed by B. Foltmann et al (*J. Biol. Chem.* 254, 847–8456 [1979]) are most likely the products of two different alleles of the rennin gene. Furthermore, the bovine genomic copy of the rennin gene contains intervening sequences, and in that respect the genomic copy is different from our cloned cDNA gene which is identical to the messenger RNA for pre-prorennin.

6. Expression of pre-prorennin in *E. coli*

A plasmid, pCGE5, designed to facilitate obtaining expression of pre-prorennin in *E. coli* was constructed by ligation of three agarose gel-purified segments of DNA. The plasmid pBR322 (4.5 µg) was cut with restriction endonucleases Hind III (N.E. Biolabs, 6 units) and Pst I (N.E. Biolabs, 3 units) for one hour at 37° C. in a 50 µl reaction containing 50 mM NaCl, 7 mM Tris.HCl pH 7.5, 7 mM MgCl$_2$ and 6 mM 2-mercaptoethanol. Double-stranded RFI DNA from recombinant phage 293-207 (4 µg) was cut with the restriction endonuclease Kpn I (N.E. Biolabs, 10 units) for one hour at 37° C. in a 50 µl reaction containing Buffer K (6 mM NaCl, 6 mM Tris.HCl pH 7.5, 6 mM MgCl$_2$, and 6 mM 2- mercaptoethanol). About 4.5 µg of DNA from plasmid pLG400 (L. Guarente, G. Lauer, T. Roberts, M. Ptasne, *Cell* 20, 543–553 1980) was cut with Hind III (N.E. Biolabs 6 units) for one hour at 37° C. in a 50 µl reaction containing Buffer H (60 mM NaCl, 7 mM Tris.HCl pH 7.5, 7 mM MgCl). After phenol extraction, ether extraction, and ethanol precipitation, the cut DNA from 293-207 and pLG400 were separately treated with T$_4$ DNA polymerase (P-L Biochemicals, 10 units) for 30 minutes at 37° C. in a 50 µl reaction containing Buffer T (25 mM Tris.HCl pH 8, 6.6 mM MgCl$_2$, 5 mM 2-mercaptoethanol, 0.5 mM EDTA, and 0.5 mM of each deoxynucleotide triphosphate) in order to create blunt ends at the restriction cuts. After phenol extraction, ether extraction and ethanol precipitation, the pLG400 DNA was further cut with Pst I (N.E. Biolabs, 3 units) for two hours at 37° C. in 50 µl of Buffer P (50 mM NaCl, 7 mM Tris.HCl pH 7.5, 7 mM MgCl$_2$, and 6 mM 2-mercaptoethanol) while the 293-207 DNA was cut with Hind III (N.E. Biolabs, 6 units) for two hours at 37° C. in 50 µl of Buffer H. Each of the three preparations of restriction cut DNA was phenol extracted, ether extracted, and ethanol precipitated, and redissolved in 30 µl H$_2$O and applied to a preparative horizontal 1% agarose gel. After electrophoresis for 3–4 hours at 70–80 volts in 40 mM Tris.acetate pH 7.2, the gel was stained with ethidium bromide and examined under long wavelength ultraviolet light. The 500 base pair (bp) band from 293-207, the 6000 bp band from pLG400, and the 800 bp band from pBR322 were excised and the DNA extracted by freezing and thawing the gel pieces (Thuring et al, *Anal. Biochem.* 66, 213 [1975]). All three DNA segments were ethanol precipitated and redissolved in H$_2$O. Approximately 0.15 pmoles of each piece was ligated together overnight at 14° C. in a 20 µl reaction containing Buffer L (66 mM Tris.HCl pH 7.5, 6.7 mM MgCl$_2$, 10 mM dithiothreitol, 0.75 mM ATP) and T$_4$ DNA ligase (N.E. Biolabs, 600 units). Transformation-competent *E. coli* strain CGE6 cells were prepared exactly as described in Section 4, and 5 µl of the ligated DNA in 50 µl of 50 mM Tris.HCl pH 7.6 was mixed with 100 µl of the cells for one hour at 0° C., heat treated at 37° C. for two minutes, and diluted ten-fold with fresh tryptone broth. After incubation for one hour at 37° C. with shaking, cells were plated on tryptone plates containing ampicillin (20 µg/ml). Ampicillin-resistant colonies were picked, and the plasmid DNA was prepared and analyzed by restriction enzyme digestion. By these criteria several strains carried the desired plasmid, pCGE5 FIG. 1. DNA sequence analysis revealed that the junction between 293-207 DNA and pLG400 DNA was as expected, and thus, the 5' end of the pre-prorennin is fused in frame to the 3' end of the I"Z fusion of Guarente et al. Plasmid DNA was prepared from a strain carrying pCGE5 by standard methods (D. B. Clewell and D. R. Helinski, *Pro. Nat. Acad, Sci. USA* 62 1159–1166 [1969]).

A DNA fragment carrying the lactose operon promoter and ribosome binding site was isolated from plasmid pGL101 (L. Guarente, G. Lauer, T. Roberts and M. Ptashne, *Cell* 20 543–553 [1981]) by cutting 10 µg of the DNA with Pvu II (N.E. Biolabs, 7.5 units) and Pst I (N.E. Biolabs, 4 units) for two hours at 37° C. in 100 µl reaction containing Buffer P. The 850 bp segment was isolated from a preparative agarose gel by excision of the band and freeze/thaw as described above.

Figure 2:
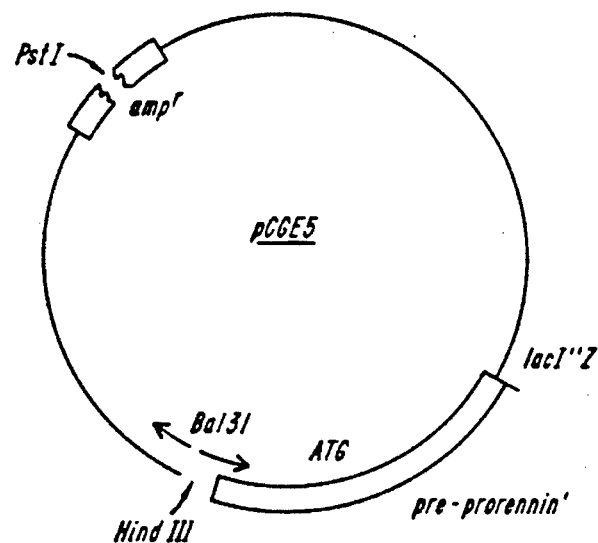
FIG. 2 is a schematic representation of plasmid pCGE 5 which has been cut with Hind III, partially digested with Bal31, treated with $T_4$DNA polymerase and then partially digested with PstI.
Figure 3:
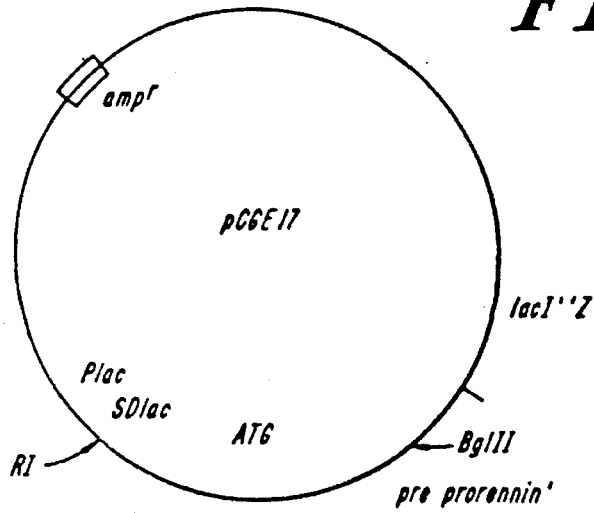
FIG. 3 is a schematic representation of plasmid pCGE 17.

Plasmid pCGE5 DNA (40 μg) was cut with Hind III (CRI, 70 units) for one hours, at 37° C. in a 150 μl reaction containing Buffer H (see above). This DNA was next digested with the exonuclease Bal 31 (N.E. Biolabs, 5 units) for 10 minutes at 30° C. in a 200 μl reaction containing Buffer B (0.6M NaCl, 12 mM CaCl$_2$, 12 mM MgCl$_2$, 20 mM Tris.HCl pH8, and 1 mM EDTA) (see FIG. 2). Analysis by gel electrophoresis indicated that the Bal 31 treatment removed a sufficient number of nucleotides to yield a set of fragments having 5' ends near the ATG initiation codon for pre-prorennin. The DNA was rendered blunt ended as described above using T$_4$ DNA polymerase, and then the DNA (1 μg) was partially digested with Pst I (N.E. Biolabs, 0.06 units) for 5 minutes at 37° C. in a 20 μl reaction containing Buffer P. Next, this DNA was ligated together with the 850 bp DNA fragment carrying the lactose operon promoter and ribosome binding site (0.2 μg) in a 20 μl reaction containing T$_4$ DNA ligase (CRI, 300 units) in Buffer L. Transformation-competent cells of *E. coli* strain CGE7 (NK5031, suIII$^+$, lac∇M5265, nal$^r$, F$^-$, B1$^-$) were prepared exactly as described above for strain CGE6, and 100 μl of the cells in suspension were transformed with 5 μl of the reaction mix, incubated, heat shocked and grown for phenotypic expression of ampicillin resistance exactly as described above for CGE6 transformation with pCGE5. The cells were plated on MacConkey lactose plus ampicillin (20 μg/ml) medium. Dark red colonies, expressing β-galactosidase were picked and assayed for β-galactosidase activity (J. Miller, Experiments in Molecular Genetics New York, Cold Spring Harbor Laboratory 1972). The plasmid DNA was isolated from twelve of these transformants, and analyzed by restriction enzyme digestion and agarose or polyacrylamide gel electrophoresis. One strain, CGE20, bears the lactose operon promoter about 40 nucleotides from the ATG initiation codon of the pre-prorennin-I"Z fusion on plasmid pCGE17 (see FIG. 3) and produces intermediate levels of β-galactosidase (about ⅓ of the fully induced level of a lactose$^+$ strain such as CGE6).

Figure 4:
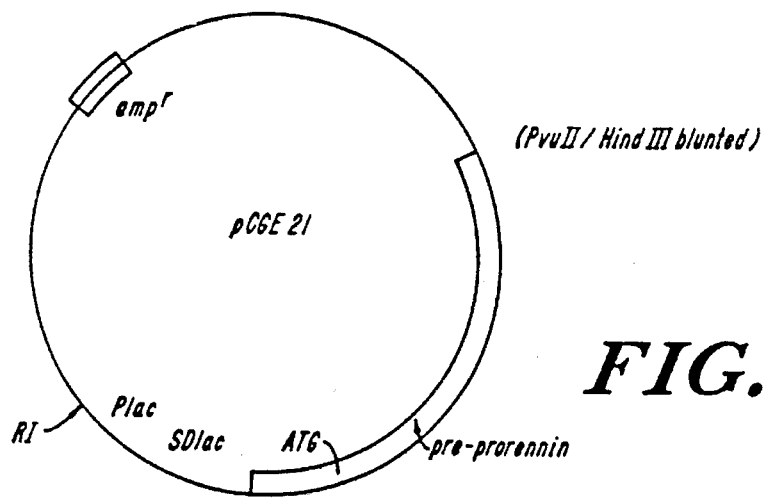
FIG. 4 is a schematic representation of plasmid pCGE 21.

In order to create a plasmid bearing the entire pre-prorennin gene fused to the lactose promoter and ribosome binding site, pCGE17 DNA (4 μg) was cut with Bgl II (N.E. Biolabs, 6 units) for one hour at 37° C. in a 90 μl reaction containing Buffer P. Then, Tris.HCl pH 7.5 was added to 100 mM and the DNA was further cut with EcoRI (Boehringer/Mannheim, 40 units) for an additional hour at 37° C. Next, pBR322 DNA (5 μg) was cut with Pvu II (N.E. Biolabs, 5 units) for one hour at 37° C. in a 45 μl reaction containing Buffer P, followed by addition of Tris.HCl pH 7.5 to 100 mM and addition of EcoRI (Boehringer/Mannheim, 40 units) with further incubation at 37° C. for one hour. Finally, recombinant f1 phage 293-118/37 RFI DNA (6 μg) was cut with Hind III (N.E. Biolabs, 6 units) for one hour at 37° C. in a 50 μl reaction containing Buffer H. After phenol extraction and ethanol precipitation, the cut DNA was treated with T$_4$ DNA polymerase (P-L Biochemicals, 10 units) at room temperature for 30 minutes in a 50 μl reaction containing Buffer T to blunt the Hind III site. Then, the redissolved phenol-extracted and ethanol precipitated DNA was cut with Bgl II (N.E. Biolabs, 4 units) for one hour at 37° C. in a 30 μl reaction containing Buffer P. The three restriction cut DNA species were applied to a preparative horizontal agarose gel, and the 370 bp pCGE17 piece, the 2300 bp pBR322 piece and the 1000 bp 293-118/37 piece were excised and eluted by freezing and thawing the agarose chunk. After ethanol precipitation, the DNA was redissolved in water and about 0.2 pmoles of each piece were ligated together for six hours at 14° C. in a 20 μl reaction containing Buffer L and T$_4$ DNA ligase (N.E. Biolabs, 300 units). *E. coli* strain CGE6 was transformed with the ligated DNA as described above and ampicillin resistant colonies were picked. Analysis of the plasmid DNA by restriction enzyme cleavage revealed strain CGE24 carries the plasmid pCGE21 (see FIG. 4) which bears the entire pre-prorennin sequence fused to the lactose operon promoter and ribosome binding site.

Two kinds of analysis reveal that this strain is synthesizing authentic calf pre-prorennin. First, crude extracts of the cells inhibit binding of iodinated rennin to anti-rennin serum in a radioimmune assay performed according to the method of Peak et al (G. J. Peak, J. Morris and M. J. Buckman [1979] "Growth Hormones" in Methods of Hormone Radioimmunoassay pp. 223–244 [B. M. Jaffe & H. R. Behrman, eds.] Academic Press, New York) with the following modifications: iodinated rennin is stored in 50 mM Sodium Phosphate pH6., 0.15M NaCl, 1% BSA; RIA buffer is 0.05M Tris.HCl pH 8, 0.5% human serum albumin and 0.1% sodium nitrite; incubation is at 4° C. for 18 hours. The amount of inhibition indicates about 0.8 μg of pre-prorennin is present in each milliliter of extract (or about 4 μg of pre-prorennin per liter of cell culture). Second, cells were pulse labelled for 30 minutes in mid-exponential phase with $^{35}$S-methionine, lysed and immunoprecipitated with anti-rennin serum (as described by J. S. Emtage et *Nature* 283 171–175[1980]). When the immunoprecipitates were analyzed on a 10% polyacrylamide gel containing SDS (U.K. Laemmli & M. Favre, *J. Mol Biol.* 80 575–599 [1973]) and autoradiographed, a band approximately the size of pre-prorennin was observed. In addition, a band the size of rennin was also observed, suggesting the bacteria may be processing the pre-prorennin to rennin, or a second initiation of translation may occur within the pre-prorennin sequence. Neither band was present in immunoprecipitates of the parent strain CGE6 which contains no plasmid. These results show that pre-prorennin is produced in *E. coli* cells carrying the plasmid pCGE21, and the level of production is about 600 molecules per cell. Higher levels of production will be possible using this same scheme by obtaining fusions of the lactose operon promoter closer to the initiation codon of pre-prorennin.

Extracts of strain CGE24 were also tested for activity in the standard milk-clotting assay of B. Foltmann (*Methods in Enzymology* [1970] 19, 421–436). The results indicate that this *E. coli* strain produces about 100 molecules per cell of active rennin or an active fragment of rennin capable of clotting milk, while an extract from strain CGE6 which contains no rennin DNA sequences is incapable of clotting milk. Strain CGE24 bearing plasmid pCGE21 is on deposit with the American Type Culture Collection (ATCC) Accession No. 31929.

Figure 5:
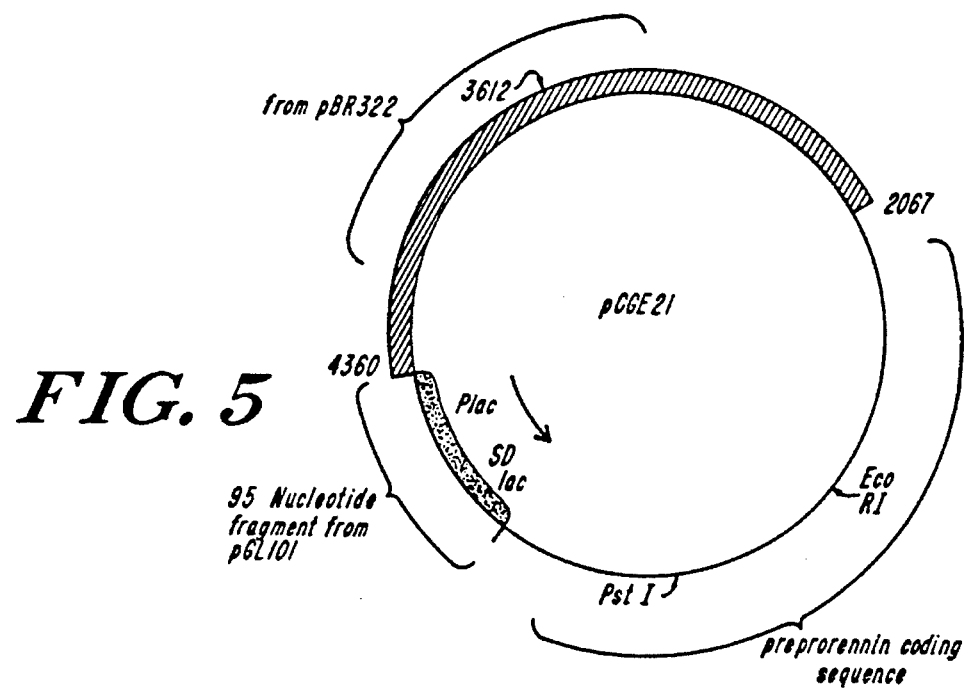
FIG. 5 is another schematic representation of plasmid pCGE 21.

Strain CGE24 is *E. coli* strain BNN45 (hsdR$^-$ hsdM$^+$ supE44 supF B1$^-$ met$^-$) (*Advanced Bacterial Genetics*, R. W. Davis, D. Botstein, J. R. Roth, Cold Spring Harbor Laboratory, Cold Spring Harbor, N.Y. 1980 p. 7) carrying the plasmid pCGE21 which is defined by FIG. 5. The plasmid contains a portion of the plasmid pBR322 (nucleotides 2067 to 4360, see J. G. Sutcliffe [1979] Cold Spring Harbor Symposium 43, 77–90) and a 95 base pair fragment bounded by EcoRI and PvuII sites from plasmid pGL101 (L. Guarente, G. Lauer, T. M. Roberts and M. Ptashne [1980] *Cell* 20, 543–553) fused to about 1300 nucleotides which code for the pre-prorennin molecule (from recombinant f1 phage 293-208 and 293-118/37). The orientation is such that the lactose operon promoter drives expression of the pre-prorennin protein in *E. coli*.

7. Expression of Methionine Prorennin in *E. coli*

The pre-prorennin gene contains three recognition sites for the restriction endonuclease Hha I (recognizes GCGC [see Table 1]), one of which removes the "pre" signal sequence and leaves the sequence for prorennin minus the first nucleotide (G) for the alanine codon. Accordingly, we isolated this partial HhaI digestion product which represents a nearly intact prorennin gene. Eighteen μg of RFI double-stranded DNA from recombinant phage 293-118/37 was cut with 12 units of restriction endonuclease Hind III (N.E. Biolabs) in 50 μl of Buffer H for one hour at 37° C. The approximately 1230 bp insert bearing rennin DNA was purified by extracting the DNA from the appropriate band on a 1% agarose gel by the freeze/thaw method. About 1.5 μg of this DNA was subjected to partial HhaI cleavage by incubation at 37° C. for 5 minutes with 0.25 units of HhaI (N.E. Biolabs) in 30 μl of Buffer P. DNA which corresponds to the uncut plus the singly cut piece missing about 25 nucleotides from the beginning of 293-118/37 was isolated from a band on a 2% agarose gel. Plasmid pBR322 DNA (10 μg) was cut with restriction endonuclease Hind III (N.E. Biolabs, 9 units) in 100 μl of Buffer H for one hours at 37° C. The DNA was phenol extracted and ethanol precipitated. About 0.5 pmoles of each DNA (i.e., the partial HhaI cut 293-118/37 and the Hind III cut pBR322) were combined, with redissolved in 28 μl of water, and rendered blunt ended by treatment with DNA polymerase I (Boehringer/Mannheim, 9 units) in a 40 μl reaction containing Buffer D (60 mM Tris.HCl pH 7.5, 8 mM $MgCl_2$, 10 mM dithiothreitol, 1 mM ATP and 0.2 mM of each deoxynucleotide triphosphate) for ten minutes at 10° C. A synthetic oligonucleotide bearing an Xba I restriction endonuclease sequence plus an ATGG (i.e., CCATCTAGATGG) was synthesized by the triester method (K. Itakura et al *J. Biol. Chem.* 250 4592 [1975]) by Collaborative Research, Inc. and 5 μg was kinased with $\alpha^{32}$-P-ATP using 6 units of $T_4$ polynucleotide kinase (P-L Biochemicals) in a 25 μl reaction containing Buffer Y (70 mM Tris.HCl pH 7.6, 10 mM $MgCl_2$, 10 mM 2-mercaptoethanol and 2 nmoles ATP). This 5'-labelled oligonucleotide was added to the 40 μl blunt-end reaction along with additional buffer components to keep the concentration constant plus 600 units of $T_4$ DNA ligase (N.E. Biolabs). The reaction was incubated at 14° C. overnight, and then diluted with five volumes of a solution of 180 mM NaCl, 7 mM $MgCl_2$ and 5 mM Tris.HCl pH 8. After heating at 65° C. for five minutes, the DNA was treated with 45 units of Xba I restriction endonuclease (15 units added each hour for a total of three hours of digestion). Finally, the oligonucleotide monomers were separated from the large DNA by gel filtration over a Bio-gel A-5m column (0.68×36 cm, see above). The excluded DNA was pooled, ethanol precipitated, redissolved in 12 μl of water and incubated in a ligation reaction containing Buffer L plus 300 units $T_4$ DNA ligase (N.E. Biolabs) at 14° C. overnight. Five microliters of this ligation reaction was used to transform competent cells of strain CGE6 as described above. The transformed cells were plated on tryptone plates containing 20 μg/ml ampicillin, and ampicillin-resistant colonies were picked and screened for tetracycline sensitivity. Analysis of the plasmid DNA by restriction enzyme digestion (Xba I plus Kpn I) and polyacrylamide gel electrophoresis revealed one strain carrying the desired plasmid pCGE 181 (i.e., gives a 250 bp Xba I-Kpn I fragment).

About 5 μg of the pCGE 181 DNA will be cut with Xba I (N.E. Biolabs, 4 units) for one hour at 37° C. in a 50 μl reaction containing Buffer X (150 mM NaCl, 6 mM Tris.HCl pH 7.9, 6 mM $MgCl_2$). After phenol extraction and ethanol precipitation, the DNA is to be rendered blunt ended by treatment with $T_4$ DNA polymerase (P-L Biochemicals, 10 units) for 30 minutes at 37° C. in a 50 μl reaction containing Buffer T. Again, the DNA will be phenol extracted, and ethanol precipitated. Vector DNA is prepared by cutting 5 μg of plasmid pGL101 DNA (L. Guarente et al *Cell* 20 543–553 [1980]) with Pvu II (N.E. Biolabs, 5 units ) in a 50 μreaction containing Buffer P. Then, after phenol extraction and ethanol precipitation, the redissolved DNA will be phosphatased by treatment with 0.06 units calf intestinal alkaline phosphatase (Boehringer/Mannheim) for 30 minutes at 37° C. in a 50 μl reaction containing Buffer C. The Pvu II-cut vector (0.2 pmoles) and the Xba I-cut prorennin DNA piece (0.2 pmoles) will be ligated together overnight at 14° C. in a 20 μl reaction containing Buffer L. Transformation-competent cells of strain CGE6 are prepared as described above and will be transformed with 5 μl of the ligation reaction. The resulting cells are plated on tryptone agar plates containing 20 μg/ml ampicillin. Ampicillin-resistant colonies will be picked, and the plasmid DNA isolated and analyzed by restriction enzyme digestion and agarose gel electrophoresis. A strain will be found which bears the prorennin DNA ligated to the lactose operon promoter and ribosome binding site such that prorennin protein will be made in vivo (i.e., the ATG initiation codon added to the prorennin sequences is nine nucleotides form the lactose operon ribosome binding site). We will determine the amount of prorennin synethesized by subjecting a lysate of cells carrying the plasmid to radioimmunoassay using iodinated authentic purified rennin and anti-rennin serum. The size of the prorennin product will be determined by electrophoresis of immunoprecipitates of $^{35}$S-methionine labelled cell extracts on SDS-containing polyacrylamide gels.

8a. Expression of Methionine-Valine-Rennin in *E. coli*

In order to obtain DNA carrying only the rennin coding sequence, the RFI DNA from recombinant phage 293-207 was resected with the nuclease Bal 31 and ligated into an f1 phage vector. The ligation products were cloned, and a library of resected rennin DNA was prepared. Specifically, 8 μg of 293-207 phage RFI DNA was cut with 6 units Hind III (N.E. Biolabs) in a 20 μl reaction containing Buffer H for one hour at 37° C. After phenol and ether extraction and ethanol precipitation, the DNA was redissolved in 20 μl of water and treated with 1.25 units Bal 31 (N.E. Biolabs) in a 50 μl reaction containing Buffer B for 30 minutes at 30° C. The reaction was stopped by phenol extraction and ethanol precipitation. Bal 31 resected DNA fragments in the size range 500–1000 bp were isolated from a 1.5% agarose gel by the freeze/thaw technique referred to above. The resected DNA was rendered blunt ended by treatment with DNA polymerase I (Boehringer/Mannheim, 9 units) in a 40 μl reaction containing Buffer D for 10 minutes at 10° C. Synthetic oligonucleotide linkers (specifically, Hind III 8-mer CAAGCTTG; 5.0 μg from Collaborative Research, Inc.) were kinased with $^{32}$P-ATP using 6 units of $T_4$ polynucleotide kinase (P-L Biochemicals) in a 25 μl reaction containing Buffer Y. This labelled oligonucleotide was added to the 40 μl blunt-end reaction along with additional buffer components to keep the concentration constant plus 600 units $T_4$ DNA ligase (N.E. Biolabs). The reaction was incubated at 14° C. overnight. Next, the reaction was diluted five-fold with 250 µl of a 60 mM NaCl plus 7 mM MgCl$_2$ solution and heated at 65° C. for 5 minutes. After cooling of the reaction mix, a total of 45 units of Hind III restriction endonuclease (N.E. Biolabs) was added, 15 units each hour for a total of three additions and three hours incubation at 37° C. The oligonucleotide linker monomers were removed from the mixture by elution over a Biogel A-5m column (0.68×36 cm, Bio Rad) in column buffer (10 mM Tris.HCl pH 7.5, 100 mM NaCl, 1 mM EDTA). The excluded peak was ethanol precipitated, and the DNA (about 0.5 pmoles) was added to a 20 µl ligation reaction containing Buffer L. 600 units T$_4$ DNA ligase (N.E. Biolabs) and about 0.5 pmoles phage CGF4 RFI DNA (Collaborative Genetics Inc.) which had been cut with Hind III and phosphatased as described above. After ligation at 14° C. for 18 hours, 4 µl of a 40-fold dilution of the reaction mix in 50 mM Tris.HCl pH 7.6 was used to transfect competent cells of strain CGE6. The transfection and plating for plaques was carried out exactly as described in Section 4 above. About 500 plaques were obtained per plate; probing by the method of Benton and Davis (*Science* 196 180–182 [1977]) using nick-translated pre-prorennin DNA carried on plasmid pBR322 (method of P. W. J. Rigby et al [1977]*J. Mol. Bio.* 113 237–251) revealed about 15% of the plaques carried rennin DNA. About 250 of these were picked and stored in tryptone broth at 4° C. Analysis of the DNA from several of these recombinant phage by restriction enzyme digestion and agarose gel electrophoresis will reveal several phage bearing Bal 31-resected pre-prorennin DNA such that the 5' end of the inserted sequence is close to the beginning of the rennin coding sequence (i.e., nucleotide 379 in the sequence given in Table 1). Single-stranded recombinant f1 phage DNA is isolated from these phage as follows. First, a plate stock of phage is prepared by infecting 0.4 ml of an overnight culture of CGE5 with 50 µl of phage picked from a plaque. This is poured onto a 150 mm tryptone agar plate in 7 ml of 0.7% soft agar. The phage are eluted after overnight growth by adding 12 ml tryptone broth to the plate and incubating 2 hours. Three ml of that broth is then precipitated with 0.6 ml of a polyethylene glycol/NaCl solution (25% PEG and 2.5M NaCl) and stored at 4° C. for one hour (K. R. Yamamoto et al *Virology* 40 734–744 [1970]). After centrifugation, the phage are resuspended in 0.3 ml Buffer TEN (10 mM Tris.HCl pH 8, 10 mM NaCl, 0.5 mM EDTA). Then the phage are precipitated with 30 µl of the PEG/NaCl solution, incubated for one hour at 4° C. and centrifuged. The phage are resuspended in 50 µl Buffer TEN and 5.5 µl of 1% SDS is added to each tube. After 55° C. incubation for 10 minutes, 200 µl TEN is added and the solutions are phenol extracted, either extracted and ethanol precipitated. The sequence of the inserted DNA in the recombinant f1 phage may be determined by the method of Sanger (F. Sanger et al *J. Mole. Biol.* 143 161–178 [1980]) using a synthetic oligonucleotide primer (a "universal primer" with the sequence TTGACGGGGAAAG, Collaborative Research, Inc., Waltham, Mass.). From the collection of Bal 31-resected inserts cloned in f1, at least one phage will be found, to be called (293-207-101), which bears the Hind III linker fused to the 5' end of rennin at nucleotide 379 (i.e., at the codon for glycine which is the N-terminal amino acid of mature rennin). The RFI DNA (5 µg) of the phage 293-207-101 will be digested with Hind III (4 units, N.E. Biolabs) for one hours at 37° C. in a 50 µl reaction containing Buffer H. After phenol extraction and ethanol precipitation, the DNA will be redissolved in 20 µl water and treated with 10 units of nuclease S1 (Boehringer/Mannheim) at 37° C. for 10 minutes in a 50 µl reaction containing Buffer S (see Section 2 above). This DNA is again phenol extracted and ethanol precipitated. Next, synthetic oligonucleotide linkers (with the sequence, CCATCTAGATGG, 5 µg, Collaborative Research, Inc.) are kinased with α-$^{32}$P-ATP using 6 units of T$_4$ polynucleotide kinase (P-L Biochemicals) in a 25 µl reaction containing Buffer Y. This kinased oligonucleotide will be ligated onto the Hind III-bound insert which had been S1-treated (as described above) and purified from an agarose gel by the freeze/thaw method. The ligation mixture will contain about 0.8 pmoles Hind III-bounded S1-treated rennin DNA, 100 pmoles kinased synthetic linker and 600 units T$_4$ DNA ligase (N.E. Biolabs) in 20 µl Buffer L. Incubation is at 14° C. for 18 hours. The reaction will be diluted six-fold with 100 µl of a solution of 180 mM NaCl, 7 mM MgCl$_2$ and 5 mM Tris.HCl pH 8. After heating at 65° C. for 5 minutes, 45 units of restriction endonuclease Xba I (N.E. Biolabs) will be added in three additions of 15 units each during a three hour incubation at 37° C. Oligonucleotide monomers are to be separated from the large DNA by gel filtration over a Biogel A-5m column (0.68×36 cm) in column buffer (see above). The excluded DNA is ethanol precipitated and subjected to T$_4$ DNA polymerase ((P-L Biochemicals, 10 units) treatment in 50 µl of Buffer T to blunt the Xba-cut ends. After phenol extraction and ethanol precipitation the DNA will be subjected to Eco RI (N.E. Biolabs, 4 units) digestion for one hour at 37° C. in a 50 µl reaction containing Buffer R (100 mM Tris.HCl pH 7.5, 50 mM NaCl, 5 mM MgCl$_2$). The rennin fragment (about 350 bp) may be isolated from a 2% agarose gel. Phage 293-118/37 RFI DNA (5 µl) will be cut with Hind III (N.E. Biolabs, 4 units) for one hour at 37° C. in a 50 µl reaction containing Buffer H. After phenol extraction and ethanol precipitation, the DNA should be blunt-ended at 37° C. for 30 minutes using T$_4$ DNA polymerase (P-L Biochemicals, 10 units) in 50 µl Buffer T. Next, following another phenol extraction and ethanol precipitation, the DNA will be cut with Eco RI (N.E. Biolabs, 4 units) for one hour at 37° C. in a 50 µl reaction containing Buffer R. This Eco RI to Hind III (blunt) DNA fragment from phage 293-118/37 (about 660 bp) will be isolated from a 2% agarose gel. Plasmid DNA (5 µg) from plasmid pGL101 is cut with Pvu II (N.E. Biolabs, 4 units) for one hour at 37° C. in 50 µl of Buffer P, and then the DNA will be phenol extracted and ethanol precipitated. After treatment with calf intestinal alkaline phosphatase (0.1 unit, Boehringer/Mannheim) in 50 µl of Buffer C, the DNA is again phenol extracted and ethanol preicpitated. A ligation reaction will be carried out at 14° C. for 18 hours using 0.2 pmoles of the linkered-rennin DNA (nucleotide 379–731), 0.2 pmoles of rennin DNA from phage 293-118/37 (nucleotide 732–1456) and 0.2 pmoles of Pvu II cleaved pGL101 in 20 µl of Buffer L using 300 units T$_4$ DNA ligase (N.E. Biolabs). Five microliters of the reaction may be used to transform 100 µl of Ca$^{++}$-treated CGE4 cells (as described above). Restriction endonuclease analysis of plasmid DNA from several ampicillin-resistant colonies picked from tryptone plates with 20 µg/ml ampicillin will reveal one colony with a plasmid, pCGE188, which carries the rennin sequence in proper orientation to be expressed off the lactose operon promoter.

We will determine the amount of rennin synthesized by subjecting a lysate of cells carrying the plasmid to radioimmune assay using iodinated authentic purified rennin and anti-rennin serum. The size of the rennin product will be determined by electrophoresis of immunoprecipitates of $^{35}$S-methionine labelled cell extracts on SDS-containing polyacrylamide gels.

In addition, the amount of active rennin present in the *E. coli* cell extracts will be measured using a modified microscale version of the standard milk-clotting assay (B. Foltmann *Methods in Enzymology* 19 pp 421–436 [1970]).

8b. Expression of Methionine-Rennin A in *E. coli*

A plasmid containing the nucleotide sequence of the rennin A gene immediately preceded by the initiation codon ATG and under the control of the lac operon promoter may be constructed as described below. This construction requires the creation of three separate plasmids which will be used in stepwise recombination to produce the final product.

The first plasmid to be made is one containing the initiation codon ATG immediately preceding the first approximately 350 nucleotides of the rennin gene. Double-stranded recombinant f1 phage 293-118/37 DNA (200 µg) was digested with the restriction endonuclease PstI (N.E. Biolabs, 20 units) for 150 minutes at 37° C. in a 100 µl reaction containing Buffer P. Eleven microliter of 100 mM Tris.HCl pH 7.5 and 4 µl of EcoRI (Boehringer/Mannheim, 80 units/µl) were added, and the digestion was continued at 37° C. for 60 additional minutes. Restriction was terminated by addition of 1/10 volume of 200 mM EDTA and DNA restriction fragments were separated by agarose gel electrophoresis in a 0.6% agarose gel containing 40 mM Tris.acetate pH 8.3. The gel was stained with ethidium bromide (0.5 µ/ml), and that portion containing the desired 400 bp band was visualized under long wavelength ultraviolet light and excised. DNA was separated from the gel by the freeze-thaw method and ethanol precipitated. The DNA was redissolved in water and digested with the restriction endonuclease MspI (N.E. Biolabs, 30 units) for one hour at 37° C. in a 50 µl reaction containing 10 mM Tris.HCl pH 7.4, 120 mM MgCl$_2$, 6 mM KCl and 1 mM dithiothreitol. This reaction produced a fragment containing the sequence 5' C GGC TTC $\overline{\text{GGG}}$ GAG ...

CG AAG CCC CTC ... 5' near the beginning of the rennin gene (the first codon of the rennin gene sequence is overscored, and represents nucleotides 379–381 Table 1). After phenol extraction, ether extraction, and ethanol precipitation, this fragment and two small fragments produced by MspI digestion were treated with the Klenow fragment of *E. coli* DNA polymerase I (Boehringer/Mannheim, 3 units) for 15 minutes at 37° C. in a 42 µl reaction containing 0.05 mM deoxyadenosine triphosphate, 6.6 mM Tris.HCl pH 7.5, 6.6 mM NaCl, 6.6 mM MgCl$_2$ and 6.6 mM dithiothreitol. This reaction trimmed two nucleotides from the above sequence to produce 5'C GGC TTC $\overline{\text{GGG}}$ GAG ...

AAG CCC CTC ... 5'

After phenol extraction and ether extraction the deoxyadenosine triphosphate was separated from the larger molecular weight species by the addition of 0.5 µl of 200 mM spermine, incubation on ice for 15 minutes, centrifugation for 10 minutes in a 4° C. microcentrifuge, and centrifugation of the resulting pellet twice for five minutes each at 4° C. in the presence of 75% ethanol. The spermine was removed by the addition of 1 ml 75% ethanol. 0.3M sodium acetate, and 10 mM magnesium acetate to the pellet, followed by one hour incubation on ice, and centrifugation as just described.

A second treatment of the DNA with the Klenow fragment of *E. coli* DNA polymerase I was conducted as described above except that 0.05 mM deoxycytidine triphosphate was substituted for the 0.05 mM deoxyadenosine triphosphate of the previous reaction. This procedure produced a fragment with the sequence 5' C GGC TTC $\overline{\text{GGG}}$ GAG ...

CCC CTC ... 5' near the beginning of the rennin gene. After phenol extraction, ether extraction, and ethanol precipitation, the DNA was redissolved in water and treated with S1 nuclease (Boehringer/Mannheim, 100 units) for 30 minutes at room temperature in a 50 µl reaction containing Buffer S. This enzyme removed the 5' single-stranded DNA from the fragment leaving the sequence 5' $\overline{\text{GGG}}$ GAG ...

CCC CTC ... 5'

Thus, the beginning of the rennin sequence is at the 5' end of the DNA fragment. A synthetic oligonucleotide containing a ClaI restriction site and ending with the nucleotides ATG (i.e., CATCGATG, Collaborative Research, Inc., 5 µg) was kinased with $\alpha^{32}$P-ATP using T$_4$ polynucleotide kinase ((P-L Biochemicals, 3 units) for 30 minutes at 37° C. in a 25 µl reaction containing Buffer Y. This kinased linker (about 200 pmole was ligated to the treated DNA fragment (about 5 pmoles) by incubation with T$_4$ DNA Ligase (N.E. Biolabs, 900 units) at 15° C. overnight in Buffer L. The reaction was terminated by heating at 65° C. for 5 minutes. Four microliters of 10x ClaI buffer (1x=10 mM Tris.HCl pH 8, 10 mM MgCl$_2$), and 10 µl of restriction endonuclease ClaI (Boehringer/Mannheim, 27 units) were added. The resulting mixture was incubated at 37° C. for one hour. Four microliters were removed for analysis on a polyacrylamide gel, followed by the addition of 1 µl of 10x ClaI buffer, 10 µl of ClaI enzyme, and 3 µl water. This mixture was incubated for an additional hour. The treated DNA containing the desired rennin sequences was purified by separation in a 2% agarose gel containing 40 mM Tris.acetate buffer pH 8.3. The DNA was visualized by long wave ultraviolet irradiation and removed from the gel by the freeze-thaw method described above. This fragment was then ready for insertion into the appropriate vector.

Preparation of the vector DNA began with digestion of 3.3 µg of pBR322 DNA with 5.4 units of ClaI endonuclease (Boehringer/Mannheim) for one hour at 37° C. in a 30µl reaction containing ClaI buffer. After phenol extraction, ether extraction, and ethanol precipitation, the vector DNA was treated with 0.006 units calf intestinal alkaline phosphatase (Boehringer/Mannheim) at 37° C. for 15 minutes in Buffer C. After phenol extraction, ether extraction, and ethanol preceiptiation, approximately 1 pmole of vector DNA was mixed with approximately 2 pmoles of rennin fragment DNA as prepared above. These two DNA pieces were ligated together in a 29 µl reaction containing Buffer L and T$_4$ DNA ligase (N.E. Biolabs, 450 units). Transformation-competent cells of *E. coli* strain CGE43 (F$^-$∇(lac-pro)XIII, also known as strain LG90) were prepared as described in Section 4 and transformed with the ligated DNA. Ampicillin-resistant colonies selected on plates were picked, and the plasmid DNA was analyzed by restriction enzyme digestion. It will be necessary to sequence portions of these plasmids to insure that the proper construction containing the linker sequence, CATCGATG, adjacent to the beginning of the rennin gene sequence $\overline{\text{GGG}}$ GAG ...

has been obtained. The plasmid with the desired correct sequence which will be called pCGE301 will be used in conjunction with the other two plasmids described below to produce a final plasmid which will direct the expression of methionine-rennin in E. coli.

Generating the second of the three plasmids required for this construction required the subcloning of the rennin-containing Hind III fragment of recombinant phage 293-118/37 double-stranded DNA. Three micrograms of double-stranded f1 phage 293-118/37 DNA were digested with restriction endonuclease Hind III (N.E. Biolabs, 3 units) for one hours at 37° C. in a 10 μl reaction containing Buffer H plus 7 mM 2-mercaptoethanol. Four microliters of Hinc II (N.E. Biolabs, 3 units) were added and the mixture was incubated at 37° C. for an additional hour. After phenol extraction, ether extraction, and ethanol precipitation, approximately 1.5 μg of this DNA was mixed with about 1 μg of pBR322 DNA (previously treated with Hind III and calf intestinal alkaline phosphatase as previously described). The two DNA fragments were ligated together overnight at 16° C. in a 20 μl reaction containing Buffer L and $T_4$ DNA ligase (N.E. Biolabs, 600 units). Five microliters of this mixture was used to transform cells of E. coli strain CGE6, and ampicillin-resistant colonies were isolated as described above. Restriction enzyme cutting and agarose gel electrophoresis revealed the resulting plasmid, pCGE302, consists of the prorennin gene sequence from phage 293-118/37 inserted into the Hind III site of pBR322.

Generation of the third component needed for construction of the rennin-producing plasmid required digestion of 2 μg of pGL101 (L. Guarente, G. Lauer, T. M. Roberts and M. Ptashne [1980] see above) DNA with restriction endonuclease PvuII (N.E. Biolabs, 5 units) for one hour at 37° C. in a 20 μl reaction containing Buffer H plus 10 mM 2-mercaptoethanol. After phenol extraction, ether extraction, and ethanol precipitation, the DNA was mixed with a kinased synthetic oligonucleotide (CATCGATG, Collaborative Research, Inc., about 200 pmoles) and ligated with $T_4$ DNA ligase (N.E. Biolabs, 900 units) at 16° C. overnight in a 30 μl reaction containing Buffer L. The reaction was terminated by treatment at 65° C. for 5 minutes. Five microliters of this mixture was used to transform $CaCl_2$-treated cells of E. coli strain CGE43. Plasmid DNA was prepared from several transformants and subject to restriction enzyme digestion and agarose gel electrophoresis in order to identify the desired plasmid, pCGE303, which is identical to plasmid pGL101 except the PvuII site has been converted to a ClaI site.

The contruction of the final plasmid containing the ATG-rennin sequence under transcriptional control of the lac operon promoter will involve in vitro recombination of the three plasmids just described and is theoretically outlined below. Plasmid pCGE301 will be digested with restriction endonucleases KpnI and Hind III, and the resulting fragments will be treated with calf intestinal alkaline phosphatase. Plasmid pCGE302 will be digested with restriction endonucleases KpnI, Hind III and BglII. The fragments generated from these two procedures will then be mixed and ligated. This DNA will be used to transform E. coli strain CGE43. The major ampicillin-resistant plasmid product will be pCGE304, containing ATG attached to the entire rennin coding sequence.

The plasmid pCGE303 will then be digested with restriction endonucleases PstI and ClaI and treated with calf intestinal alkaline phosphatase. Plasmid pCGE304 will also be digested with PstI and ClaI. DNA fragments resulting from these two procedures will be mixed together, ligated, and used to transform strain CGE43. The ampicillin-resistant plasmids derived from the transformed cells will be analyzed by size, restriction enzyme digestion, and DNA sequence to find the desired plasmid pCGE305 which will bear the ATG-rennin sequence under transcriptional control of the lac operon promoter. This plasmid, when present in E. coli, will direct the synthesis of methionine-rennin.

9. A Method of Obtaining Expression of Pre-Prorennin, Prorennin, and Rennin is *Saccharomyces cerevisiae*

These three species, pre-prorennin, methionine-prorennin and methionine-valine-rennin may be expressed in S. cerevisiae using the promoter and other transcriptional and translational control regions from the S. cerevisiae uracil 3 gene. The yeast uracil 3 gene was placed on a plasmid (a shuttle vector which can be selected for and maintained in yeast or E. coli) in a form such that a truncated version of the β-galactosidase or lac Z gene (missing 22 bp from its 5' end) is fused to the 3' end of a fragment of the ura 3 gene (missing about 900 bp from its 3' end). This is the Class III deletion #35 reported by M. Rose, M. J. Casadaban, and D. B. Botstein in *Proc. Nat. Acad. Sci. USA* 78 2460–2464 (1981). On this plasmid, expression of the β-galactosidase activity in yeast is under control of the uracil 3 gene control regions. We will use this deletion #35 to obtain expression of pre-prorennin, methionine-prorennin, and methionine-valine-rennin in S. cerevisiae as follows.

First, a more complete deletion of the uracil 3 coding sequence will be obtained by cutting open DNA from deletion #35 with restriction endonuclease BamHI which cuts at the ura3-lacZ junction. This DNA will be resected with the nuclease Bal31 such that an average of 200 bp are removed. Next, BamHI synthetic oligonucleotide linkers (CRI) will be ligated onto the ends and the DNA will be ligated together so that a population of plasmids exists with BamHI sites at varying distances from the uracil control region. Gel electrophoresis of restriction-cut purified plasmid DNA will reveal a plasmid pCGS210 which contains very littler ura3 coding sequences. Sequencing from the BamHI site by the method of Maxam and Gilbert will confirm this. DNA from such a suitable Bal-resected cloned plasmid will be purified. This DNA will carry E. coli (ampicillin resistance) and yeast (Leu2 prototrophy) selectable marker, E. coli and yeast origins of replication, all of these being from plasmid pRB45 (M. Rose, M. J. Casadaban, D. Botstein, see above), and the ura3 control region with less than 50 nucleotides of ura3 coding material. In particular, one of these plasmids which we call pCGS210 will carry only 10–20 nucleotides of ura3 coding material as determined by DNA sequencing by the method of Maxam and Gilbert.

DNA coding of the 5' end of the pre-prorennin, prorennin and rennin will be obtained as follows. DNA coding for the pre-prorennin gene carrying the ATG translation initiation codon and less than 20 nucleotides to the 5' side of the ATG will be obtained from the Bal31-resected rennin DNA-f1 phage bank described in Section 8 above by screening those phage using restriction enzymes coupled with gel electrophoresis and sequencing by the Sanger method (F. Sanger et al *J. Mol. Biol.* 143 161–178 [1981]). DNA coding for prorennin with an ATG translation initiation codon will be obtained from plasmid pCGE181 described in Section 7 above. DNA coding for rennin with the ATG codon for translation initiation plus a GTG valine codon (phage 293-207-101) will be obtained from the rennin DNA-f1 phage bank as described in Section 8a above, or DNA coding for methionine-rennin will be obtained from plasmid pCGE304 described in Section 8b above.

In order to obtain expression in yeast of each of these pieces of DNA, the following experiments may be performed. The DNA coding for pre-prorennin, met-prorennin, met-val-rennin or met-rennin will be cut out of the appropriate phage or plasmid described above. The piece will be further cut with SmaI, and the desired fragment coding for a form of rennin will be purified by gel electrophoresis. Similarly, a BamHI (blunted) to SalI piece of DNA coding for the 'ZYA segment from *E. coli* (the gene for β-galactosidase missing 22 bp from its 5' end plus the genes for lactose permease and lactose transacetylase) will be isolated from pRB45 (M. Rose, M. J. Casadaban, and D. Botstein [1981] see above). Next, the plasmid pCGS210 described above will be cut at the unique BamHI site and resected for short distances with Bal31 nuclease (e.g. using the conditions of L. Guarente, G. Lauer, M. Ptashne [1980] see above) to yield a piece which has lost enough DNA to remove all the remaining ura3 coding sequences but not the control sequences. This DNA will also be cut with SalI, and the largest fragment will be gel purified. A trimolecular ligation reaction will be carried out using this vector fragment plus the BamHI (blunt) to SalI piece from pRB45 plus either the pre-prorennin met-prorennin or met-val-rennin DNA which was cut with SmaI and gel purified. A portion of this ligation reaction will be used to transform *E. coli* strain CGE4, and red colonies on MacConkey lactose plus ampicillin plates will be picked. Isolation and restriction enzyme analysis of the plasmid DNA will confirm the structure of the desired plasmids. Transformation into yeast strain CGY 80 (see below), selecting for leucine prototrophy and screening for blue color on minimal plus uracil (excess, or limiting amounts) plus leucine plus X-gal (5-Bromo-4-Chloro-3-indolyl-β-D-galactoside, Bachem, Calif.) medium will indicate that the plasmid directs translation of the appropriate rennin-β-galactosidase fusion protein under uracil control. Finally, the β-galactosidase coding portion of the desired plasmid will be removed by cutting the plasmid with BglII and SalI, and gel purifying the largest fragment. This piece will be ligated to the BglII to Hind III (which has been converted to a SalI site with synthetic oligonucleotide linkers, CRI) fragment from phage 293-118/37 to regenerate the complete pre-prorennin, prorennin or rennin gene. These plasmids will direct translation of pre-prorennin, met-prorennin, met-val-rennin or met-rennin in the yeast *S. cerevisiae*.

10. Expression of a Prorennin Fusion Protein in Yeast

Due to the ready availability of a plasmid pRB71 (M. Rose and D. Botstein, submitted for publication) which resembles the deletion #35 of ura3 described above (and in M. Rose, M. J. Casadaban and D. Botstein, 1981, *Proc. Nat. Acad. Sci. USA* 78 2460–2464) except only 11 nucleotides of ura3 coding material remain before the BamHI site and the lactose operon ZYA genetic material, we have constructed a plasmid pCGS28 which carries the gene for prorennin fused to the 11 nucleotides of ura3 coding material such that a fusion protein will be synthesized in *S. cerevisia*. This fusion protein consists of the authentic prorennin molecule, except the first four amino acids of prorennin have been replaced by methionine-serine-lysine-alanine. Activation to produce rennin results in the loss of the first 42 amino acids of prorennin so these initial four amino acids should have no effect on the final rennin product. The details of this plasmid construction are described below.

In order to obtain efficient expression of prorennin in yeast, the ura3 gene promoter region was used. This sequence of DNA has been cloned and is available on a plasmid (M. Rose, M. J. Casadaban and D. Botstein, 1981, *Proc. Nat. Acad. Sci. USA* 78, 2460–2464). The plasmid pRB71, obtained from M. Rose, bears the ura3 promoter region plus eleven nucleotides of the uracil 3 gene fused to a fragment of the lacZ gene missing the first 22 nucleotides. The junction between the two incomplete genes is a BamHI restriction endonuclease site. This plasmid also contains the EcoRI A fragment from the 2 um plasmid of yeast, the leu2 gene from yeast, and the origin of replication plus the ampicillin resistance gene from pBR322, as described by M. Rose et al (see above). Thus, the plasmid can be grown and its presence can be selected for in either *E. coli* or *S. cerevisiae*.

In order to obtain expression of a prorennin fusion protein (i.e., fused to the first 11 nucleotides of the ura3 gene and controlled by the ura3 promoter) in yeast, two basic plasmid constructions were generated. The first is a ura3-prorennin-lacZ fusion which when placed in yeast yields an active β-galactosidase fusion protein, indicating that the ura3 promoter is directing transcription of the desired fused genes. The second replaces the lacZ portion with the remainder of prorennin and results in yeast cells which produce a prorennin molecule bearing four amino acids specified by the ura3 gene.

In the first construction, the 5' portion of the prorennin gene was inserted into the BamHI site of pRB71 such that ura3, prorennin, and lacZ are all in the same translational reading frame. This was accomplished as follows. Double-stranded recombinant f1 phage 293-118/37 DNA (12 μg) bearing the entire prorennin gene was cut with 7 units of SmaI restriction endonuclease (N.E. Biolabs) for 2 hours at 37° C. in a 50 μl reaction containing 20 mM KCl, 6 mM Tris.HCl pH 8, 6 mM MgCl$_2$ and 6 mM 2-mercaptoethanol. The DNA was phenol extracted, ether extracted, and ethanol precipitated. Next, 250 pmoles of BamHI synthetic oligonucleotide linker (CRI, CCGGATCCGG), which had been phophorylated at the 5' end using T$_4$ polynucleotide kinase as described in Section 7 above, were ligated at 14° C. overnight to the BamHI-cut phage DNA in a 40 μl reaction containing Buffer D and 900 units T$_4$ DNA ligase (N.E. Biolabs). Following ligation, the reaction was diluted with five volumes of buffer containing 180 mM NaCl, 7 mM MgCl$_2$ and 5 mM Tris.HCl pH 8, heated at 65° C. for 5 minutes, chilled on ice and subjected to digestion for 3 hours with 15 units of BamHI endonuclease added each hour. After phenol extraction, ether extraction, and ethanol precipitation, the DNA was redissolved in water and subjected to electrophoresis in a 2% agarose gel. DNA was eluted from the band corresponding to the approximately 440 bp BamHI-SmaI(BamHI-linkered) fragment by macerating the frozen gel piece and collecting the residual liquid (freeze-thaw method). The DNA fragment was ethanol precipitated and redissolved in 6 μl water. About 5 μg of plasmid pRB71 DNA was digested with 20 units BamHI endonuclease (N.E. Biolabs) for 2 hours at 37° C. in a 50 μl reaction containing Buffer X plus 6 mM 2-mercapto ethanol. After phenol extraction, ether extraction, and ethanol precipitation, the DNA was redissolved in 20 μl water and treated with 0.1 unit calf intestinal alkaline phosphatase (Boehringer/Mannheim) for 30 minutes at 37° C. in a 50 μl reaction containing Buffer C. The phenol extracted, ethanol precipitated DNA was redissolved in 6 μl water and added to a ligation reaction containing 6 μl of the BamHI-SmaI (BamHI-linkered) fragment, and the ligation was carried out with 600 units of T$_4$ DNA ligase (N.E. Biolabs) at 14° C. overnight in 20 μl of Buffer L. Cells of *E. coli* strain CGE6 were transformed with the ligated DNA and ampicillin resistant transformants were obtained as described above. About 200 transformants were tested by the colony hybridization method of M. Grunstein and D. S. Hogness (1975, *Proc. Nat. Acad. Sci. USA*, 72, 3961–3965) using as probe α$^{32}$P-labelled nick-translated recombinant phage 293-207 DNA. Almost 20% of the transformants contained rennin sequences by this criteria. Plasmid DNA was prepared from ten of the transformants, and the orientation of the insert was determined from the pattern of fragments produced by digestion with PstI endonuclease. One of the plasmids, pCGS16, which contained the prorennin fragment in the proper orientation was used to transform *S. cerevisiae* strain CGY80 (MATa, leu2-3, leu2-112, his3, trp1-289, ura3-52) according to the protocol of A. Hinnen, J. B. Hicks and G. Fink (1978, *Proc. Nat. Acad. Sci. USA* 75, 1929–1933). Yeast transformants which were capable of growth without added leucine due to the presence of leu2 gene on the plasmid, were streaked onto minimal medium plates containing the chromogenic substrate X-gal (exactly as described by M. Rose et al see above) and supplement with uracil, tryptophan and histidine. All of the transformants examined produced blue colonies on the X-gal minimal medium indicating that β-galactosidase is produced. This means that the ura3-prorennin-lacZ fusion protein is produced and that the translational reading frame for each of the three protein fragments is the same.

This result suggested that a similar plasmid should direct the expression of a ura3-prorennin fusion protein if the β-galactosidase sequences are replaced with the remainder of the prorennin gene. Accordingly, 8 μg of plasmid pCGS16 were digested with 5 units of BglII restriction endonuclease (N.E. Biolabs) for one hour at 37° C. in 80 μl of Buffer P. Next, 10 μl 1M NaCl and 6 μl water was added to the reaction and the DNA was further digested with 16 units SalI endonuclease for one hour at 37° C. After phenol extraction, ether extraction, and ethanol precipitation, the DNA was treated with 0.06 units calf intestinal alkaline phosphatase (Boehringer/Mannheim) for 15 minutes at 37° C. in 50 μl containing Buffer C. The reaction was terminated by phenol extraction of the DNA and ethanol precipitation.

Meanwhile, about 15 μg of recombinant f1 phage 293-118/37 double-stranded DNA was cut with 12 units of Hind III (N.E. Biolabs) for 2 hours at 37° C. in 100 μl of Buffer H. After phenol and ether extraction and ethanol precipitation, the DNA (6 μg) was rendered blunt-ended by treatment with 10 units *E. coli* DNA polymerase (Boehringer/Mannheim) for 10 minutes at 10° C. in 40 μl Buffer D. Next, 250 pmoles of SalI synthetic oligonucleotide linker (CRI, GGTCGACC) which had been phosphorylated using T$_4$ polynucleotide kinase as described above was added along with sufficient buffer components to keep the concentration of all components constant. The linkers were ligated onto the DNA by incubation with 900 units of T$_4$ DNA Ligase (N.E. Biolabs) at 14° C. overnight. Next, five volumes of buffer consisting of 10 mM Tris.HCl pH 8, 10 mM MgCl$_2$ and 180 mM NaCl was added, the solution heated at 65° C. for 5 minutes, chilled on ice and then incubated for 5 hours at 37° C. with an addition of 20 units of SalI restriction endonuclease (N.E. Biolabs) each hours. After the DNA was phenol extracted, ether extracted, and ethanol precipitated, it was redissolved in 20 μl water and digested with 5 units BglII (N.E. Biolabs) for one hour 37° C. in a 30 μl volume containing Buffer P. Then the reaction was terminated with ¹⁄₁₀ volume of 200 mM EDTA and applied to a 2% agarose gel. The band corresponding to the approximately 1000 bp BglII-Hind III (SalI-linkered) fragment was excised and the DNA was recovered by the freeze-thaw method described above.

The ethanol precipitated pCGS16 DNA which had been cut with BglII and SalI endonuclease was redissolved in 13 μl water along with the gel purified 293-118/37 BglII-Hind III (SalI-linkered) DNA fragment and the two pieces were ligated together in a 20 μl reaction containing Buffer L and 600 units T$_4$ DNA ligase (N.E. Biolabs). Cells of strain CGE6 were treated with CaCl$_2$ and transformed with the ligated DNA as described above. Plasmid DNA was purified from five different ampicillin-resistant transformants and subjected to digestion with BamHI or PstI plus SalI. The positions of the bands in a 2% agarose gel indicated that the entire prorennin sequence is present in plasmid pCGS28.

Accordingly, the yeast strain CGY80 was transformed with the plasmid DNA by the method of A. Hinnen, J. B. Hicks, and G. Fink (1978, see above) and leucine prototrophs were selected. One such transformant, CGY116, was grown to exponential phase in minimal medium containing the appropriate amino acid supplements, labelled with 100 uCi $^{35}$S-L-methionine for one-half generation at 30° and lysed by vortexing with glass beads (250–300 um) for 3 minutes. The extract was clarified by centrifugation and immunoprecipitated with rennin antiserum. The immunoprecipitate was dissolved in SDS sample buffer and subjected to electrophoresis in a 10% polyacrylamide gel containing 0.1% SDS according to the method of U.K. Laemmli and M. Favre (see above). Autoradiography revealed that strain CGY116 carrying the plasmid pCGS28 directs the synthesis of a protein which reacts with rennin antiserum and is the size expected for prorennin. Furthermore, excess unlabelled rennin present during the immunoprecipitation eliminates the radioactive band otherwise present in the prorennin position. Therefore, *S. cerevisiae* strain CGY116 produces calf prorennin fused to four amino acids from the yeast ura3 gene in place of the first four amino acids of prorennin. Activation of the ura3-prorennin fusion protein by standard methods described by B. Foltman (*Methods in Enzymology* 19 421–436, 1970) should yield active rennin identical to authentic calf rennin A since the "pro" zymogen peptide (including the four "foreign" amino acids in this case) will be cleaved off during activation. Strain CGY 116 bearing plasmid pCGS28 is on deposit with the American Type Culture Collection (ATCC) and its Accession number is 20623.

Figure 6:
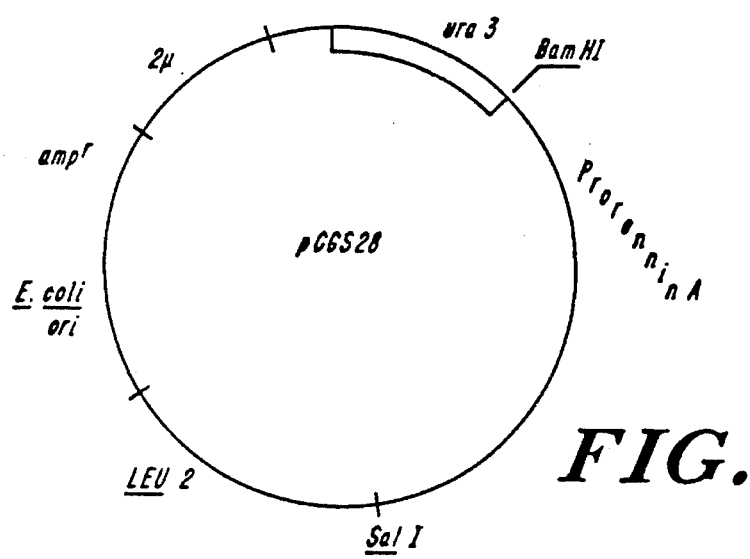
FIG. 6 is a schematic representation of plasmid pCGE 28.

Strain CGY116 is *S. cerevisiae* strain CGY80 (MAT a, leu 2–3, leu2-112, ura 3–52, his 3∇, trp 1–289, carrying the plasmid pCGS 28, which is defined as follows (and see FIG. 6). The plasmid contains most of plasmid pBR322 (J. G. Sutcliffe [1979] Cold Spring Harbor Symposium 43, 77–90), the Eco RI, A fragment of the yeast 2 μm plasmid (J. L. Hartley and J. E. Donelson [1980] *Nature* 286, 860–865), the Sal I - Xho I fragment of yeast chromosomal DNA carrying the LEU 2 gene (A. Hinnen, J. Hicks and G. R. Fink [1978] *Proc. Nat. Acad. Sci. USA*, 75 1929–1933), a fragment from the yeast chromosomal DNA consisting of a portion of the ura3 gene (from HI to a site 11 nucleotides 3' to the initiation of translation as in pRB71 plus the prorennin A gene from the BamHI site at nucleotide #267 to the end of the gene.

With reference again to Table 1, the nucleotide and amino acid sequence of preprorennin A as shown, illustrates the nucleotide sequences for several of the materials of this invention. These materials can be cut from the nucleotide sequence shown by conventional procedures. Similarly the pre-prorennin A form can be changed to the prorennin B form by substituting a glycine residue at position number 290 in place of the aspartate residue at this position. Useful products obtained from the pre-prorennin A derived by the process of this invention as shown in Table 1 include the following nucleotide sequences forming part of the recombinant DNA material:

1. A gene coding for a polypeptide displaying rennin activity having a nucleotide sequence as shown from numbers 379 to 1350 in Table 1 and repeated below GGG GAG GTG GCC AGC GTG CCC CTG ACC AAC TAC CTG GAT AGT CAG TAC TTT GGG AAG ATC
GLY GLU VAL ALA SER VAL PRO LEU THR ASN TYR LEU ASP SER GLN TYR PHE GLY LYS ILE TAC CTC GGG ACC CCG CCC CAG GAG TTC ACC GTG CTG TTT GAC ACT GGC TCC TCT GAC TTC
TYR LEU GLY THR PRO PRO GLN GLU PHE THR VAL LEU PHE ASP THR GLY SER SER ASP PHE TGG GTA CCC TCT ATC TAC TGC AAG AGC AAT GCC TGC AAA AAC CAC CAG CGC TTC GAC CCG
TRP VAL PRO SER ILE TYR CYS LYS SER ASN ALA CYS LYS ASN HIS GLN ARG PHE ASP PRO AGA AAG TCG TCC ACC TTC CAG AAC CTG GGC AAG CCC CTG TCT ATC CAC TAC GGG ACA GGC
ARG LYS SER SER THR PHE GLN ASN LEU GLY LYS PRO LEU SER ILE HIS TYR GLY THR GLY AGC ATG CAG GGC ATC CTG GGC TAT GAC ACC GTC ACT GTC TCC AAC ATT GTG GAC ATC CAG
SER MET GLN GLY ILE LEU GLY TYR ASP THR VAL THR VAL SER ASN ILE VAL ASP ILE GLN CAG ACA GTA GGC CTG AGC ACC CAG GAG CCC GGG GAC GTC TTC ACC TAT GCC GAA TTC GAC
GLN THR VAL GLY LEU SER THR GLN GLU PRO GLY ASP VAL PHE THR TYR ALA GLU PHE ASP GGG ATC CTG GGG ATG GCC TAC CCC TCG CTC GCC TCA GAG TAC TCG ATA CCC GTG TTT GAC
GLY ILE LEU GLY MET ALA TYR PRO SER LEU ALA SER GLU TYR SER ILE PRO VAL PHE ASP AAC ATG ATG AAC AGG CAC CTG GTG GCC CAA GAC CTG TTC TCG GTT TAC ATG GAC AGG AAT
ASN MET MET ASN ARG HIS LEU VAL ALA GLN ASP LEU PHE SER VAL TYR MET ASP ARG ASN GGC CAG GAG AGC ATG CTC ACG CTG GGG GCC ATC GAC CCG TCC TAC TAC ACA GGG TCC CTG
GLY GLN GLU SER MET LEU THR LEU GLY ALA ILE ASP PRO SER TYR TYR THR GLY SER LEU CAC TGG GTG CCC GTG ACA GTG CAG CAG TAC TGG CAG TTC ACT GTG GAC AGT GTC ACC ATC
HIS TRP VAL PRO VAL THR VAL GLN GLN TYR TRP GLN PHE THR VAL ASP SER VAL THR ILE AGC GGT GTG GTT GTG GCC TGT GAG GGT GGC TGT CAG GCC ATC CTG GAC ACG GGC ACC TCC
SER GLY VAL VAL VAL ALA CYS GLU GLY GLY CYS GLN ALA ILE LEU ASP THR GLY THR SER AAG CTG GTC GGG CCC AGC AGC GAC ATC CTC AAC ATC CAG CAG GCC ATT GGA GCC ACA CAG
LYS LEU VAL GLY PRO SER SER ASP ILE LEU ASN ILE GLN GLN ALA ILE GLY ALA THR GLN AAC CAG TAC GAT GAG TTT GAC ATC GAC TGC GAC AAC CTG AGC TAC ATG CCC ACT GTG GTC
ASN GLN TYR ASP GLU PHE ASP ILE ASP CYS ASP ASN LEU SER TYR MET PRO THR VAL VAL TTT GAG ATC AAT GGC AAA ATG TAC CCA CTG ACC CCC TCC GCC TAT ACC AGC CAG GAC CAG
PHE GLU ILE ASN GLY LYS MET TYR PRO LEU THR PRO SER ALA TYR THR SER GLN ASP GLN GGC TTC TGT ACC AGT GGC TTC CAG AGT GAA AAT CAT TCC CAG AAA TGG ATC CTG GGG GAT
GLY PHE CYS THR SER GLY PHE GLN SER GLU ASN HIS SER GLN LYS TRP ILE LEU GLY ASP GTT TTC ATC CGA GAG TAT TAC AGC GTC TTT GAC AGG GCC AAC AAC CTC GTG GGG CTG GCC
VAL PHE ILE ARG GLU TYR TYR SER VAL PHE ASP ARG ALA ASN ASN LEU VAL GLY LEU ALA

AAA GCC ATC TGA
LYS ALA ILE.

2. A gene coding for a polypeptide displaying pre-pro-rennin activity having a nucleotide sequence as shown from numbers 205–1350 in Table 1 and repeated below ATG AGG TGT CTC GTG GTG CTA CTT GCT GTC TTC GCT CTC TCC CAG GGC
MET ARG CYS LEU VAL VAL LEU LEU ALA VAL PHE ALA LEU SER GLN GLY GCT GAG ATC ACC AGG ATC CCT CTG TAC AAA GGC AAG TCT CTG AGG AAG GCG CTG AAG GAG CAT
ALA GLU ILE THR ARG ILE PRO LEU TYR LYS GLY LYS SER LEU ARG LYS ALA LEU LYS GLU HIS GGG CTT CTG GAG GAC TTC CTG CAG AAA CAG CAG TAT GGC ATC AGC AGC AAG TAC TCC GGC TTC
GLY LEU LEU GLU ASP PHE LEU GLN LYS GLN GLN TYR GLY ILE SER SER LYS TYR SER GLY PHE GGG GAG GTG GCC AGC GTG CCC CTG ACC AAC TAC CTG GAT AGT CAG TAC TTT GGG AAG ATC
GLY GLU VAL ALA SER VAL PRO LEU THR ASN TYR LEU ASP SER GLN TYR PHE GLY LYS ILE TAC CTC GGG ACC CCG CCC CAG GAG TTC ACC GTG CTG TTT GAC ACT GGC TCC TCT GAC TTC
TYR LEU GLY THR PRO PRO GLN GLU PHE THR VAL LEU PHE ASP THR GLY SER SER ASP PHE TGG GTA CCC TCT ATC TAC TGC AAG AGC AAT GCC TGC AAA AAC CAC CAG CGC TTC GAC CCG
TRP VAL PRO SER ILE TYR CYS LYS SER ASN ALA CYS LYS ASN HIS GLN ARG PHE ASP PRO AGA AAG TCG TCC ACC TTC CAG AAC CTG GGC AAG CCC CTG TCT ATC CAC TAC GGG ACA GGC
ARG LYS SER SER THR PHE GLN ASN LEU GLY LYS PRO LEU SER ILE HIS TYR GLY THR GLY AGC ATG CAG GGC ATC CTG GGC TAT GAC ACC GTC ACT GTC TCC AAC ATT GTG GAC ATC CAG
SER MET GLN GLY ILE LEU GLY TYR ASP THR VAL THR VAL SER ASN ILE VAL ASP ILE GLN

```
CAG ACA GTA GGC CTG AGC ACC CAG GAG CCC GGG GAC GTC TTC ACC TAT GCC GAA TTC GAC
GLN THR VAL GLY LEU SER THR GLN GLU PRO GLY ASP VAL PHE THR TYR ALA GLU PHE ASP

GGG ATC CTG GGG ATG GCC TAC CCC TCG CTC GCC TCA GAG TAC TCG ATA CCC GTG TTT GAC
GLY ILE LEU GLY MET ALA TYR PRO SER LEU ALA SER GLU TYR SER ILE PRO VAL PHE ASP

AAC ATG ATG AAC AGG CAC CTG GTG GCC CAA GAC CTG TTC TCG GTT TAC ATG GAC AGG AAT
ASN MET MET ASN ARG HIS LEU VAL ALA GLN ASP LEU PHE SER VAL TYR MET ASP ARG ASN

GGC CAG GAG AGC ATG CTC ACG CTG GGG GCC ATC GAC CCG TCC TAC TAC ACA GGG TCC CTG
GLY GLN GLU SER MET LEU THR LEU GLY ALA ILE ASP PRO SER TYR TYR THR GLY SER LEU

CAC TGG GTG CCC GTG ACA GTG CAG CAG TAC TGG CAG TTC ACT GTG GAC AGT GTC ACC ATC
HIS TRP VAL PRO VAL THR VAL GLN GLN TYR TRP GLN PHE THR VAL ASP SER VAL THR ILE

AGC GGT GTG GTT GTG GCC TGT GAG GGT GGC TGT CAG GCC ATC CTG GAC ACG GGC ACC TCC
SER GLY VAL VAL VAL ALA CYS GLU GLY GLY CYS GLN ALA ILE LEU ASP THR GLY THR SER

AAG CTG GTC GGG CCC AGC AGC GAC ATC CTC AAC ATC CAG CAG GCC ATT GGA GCC ACA CAG
LYS LEU VAL GLY PRO SER SER ASP ILE LEU ASN ILE GLN GLN ALA ILE GLY ALA THR GLN

AAC CAG TAC GAT GAG TTT GAC ATC GAC TGC GAC AAC CTG AGC TAC ATG CCC ACT GTG GTC
ASN GLN TYR ASP GLU PHE ASP ILE ASP CYS ASP ASN LEU SER TYR MET PRO THR VAL VAL

TTT GAG ATC AAT GGC AAA ATG TAC CCA CTG ACC CCC TCC GCC TAT ACC AGC CAG GAC CAG
PHE GLU ILE ASN GLY LYS MET TYR PRO LEU THR PRO SER ALA TYR THR SER GLN ASP GLN

GGC TTC TGT ACC AGT GGC TTC CAG AGT GAA AAT CAT TCC CAG AAA TGG ATC CTG GGG GAT
GLY PHE CYS THR SER GLY PHE GLN SER GLU ASN HIS SER GLN LYS TRP ILE LEU GLY ASP

GTT TTC ATC CGA GAG TAT TAC AGC GTC TTT GAC AGG GCC AAC AAC CTC GTG GGG CTG GCC
VAL PHE ILE ARG GLU TYR TYR SER VAL PHE ASP ARG ALA ASN ASN LEU VAL GLY LEU ALA

AAA GCC ATC TGA
LYS ALA ILE.
```

3. A gene coding for a polypeptide displaying prorennin activity having a nucleotide sequence as shown from numbers 253–1350 in Table 1 and repeated below

```
GCT GAG ATC ACC AGG ATC CCT CTG TAC AAA GGC AAG TCT CTG AGG AAG GCG CTG AAG GAG CAT
ALA GLU ILE THR ARG ILE PRO LEU TYR LYS GLY LYS SER LEU ARG LYS ALA LEU LYS GLU HIS

GGG CTT CTG GAG GAC TTC CTG CAG AAA CAG CAG TAT GGC ATC AGC AGC AAG TAC TCC GGC TTC
GLY LEU LEU GLU ASP PHE LEU GLN LYS GLN GLN TYR GLY ILE SER SER LYS TYR SER GLY PHE

GGG GAG GTG GCC AGC GTG CCC CTG ACC AAC TAC CTG GAT AGT CAG TAC TTT GGG AAG ATC
GLY GLU VAL ALA SER VAL PRO LEU THR ASN TYR LEU ASP SER GLN TYR PHE GLY LYS ILE

TAC CTC GGG ACC CCG CCC CAG GAG TTC ACC GTG CTG TTT GAC ACT GGC TCC TCT GAC TTC
TYR LEU GLY THR PRO PRO GLN GLU PHE THR VAL LEU PHE ASP THR GLY SER SER ASP PHE

TGG GTA CCC TCT ATC TAC TGC AAG AGC AAT GCC TGC AAA AAC CAC CAG CGC TTC GAC CCG
TRP VAL PRO SER ILE TYR CYS LYS SER ASN ALA CYS LYS ASN HIS GLN ARG PHE ASP PRO

AGA AAG TCG TCC ACC TTC CAG AAC CTG GGC AAG CCC CTG TCT ATC CAC TAC GGG ACA GGC
ARG LYS SER SER THR PHE GLN ASN LEU GLY LYS PRO LEU SER ILE HIS TYR GLY THR GLY

AGC ATG CAG GGC ATC CTG GGC TAT GAC ACC GTC ACT GTC TCC AAC ATT GTG GAC ATC CAG
SER MET GLN GLY ILE LEU GLY TYR ASP THR VAL THR VAL SER ASN ILE VAL ASP ILE GLN

CAG ACA GTA GGC CTG AGC ACC CAG GAG CCC GGG GAC GTC TTC ACC TAT GCC GAA TTC GAC
GLN THR VAL GLY LEU SER THR GLN GLU PRO GLY ASP VAL PHE THR TYR ALA GLU PHE ASP

GGG ATC CTG GGG ATG GCC TAC CCC TCG CTC GCC TCA GAG TAC TCG ATA CCC GTG TTT GAC
GLY ILE LEU GLY MET ALA TYR PRO SER LEU ALA SER GLU TYR SER ILE PRO VAL PHE ASP

AAC ATG ATG AAC AGG CAC CTG GTG GCC CAA GAC CTG TTC TCG GTT TAC ATG GAC AGG AAT
ASN MET MET ASN ARG HIS LEU VAL ALA GLN ASP LEU PHE SER VAL TYR MET ASP ARG ASN

GGC CAG GAG AGC ATG CTC ACG CTG GGG GCC ATC GAC CCG TCC TAC TAC ACA GGG TCC CTG
GLY GLN GLU SER MET LEU THR LEU GLY ALA ILE ASP PRO SER TYR TYR THR GLY SER LEU

CAC TGG GTG CCC GTG ACA GTG CAG CAG TAC TGG CAG TTC ACT GTG GAC AGT GTC ACC ATC
HIS TRP VAL PRO VAL THR VAL GLN GLN TYR TRP GLN PHE THR VAL ASP SER VAL THR ILE

AGC GGT GTG GTT GTG GCC TGT GAG GGT GGC TGT CAG GCC ATC CTG GAC ACG GGC ACC TCC
SER GLY VAL VAL VAL ALA CYS GLU GLY GLY CYS GLN ALA ILE LEU ASP THR GLY THR SER
```

-continued

```
AAG CTG GTC GGG CCC AGC AGC GAC ATC CTC AAC ATC CAG CAG GCC ATT GGA GCC ACA CAG
LYS LEU VAL GLY PRO SER SER ASP ILE LEU ASN ILE GLN GLN ALA ILE GLY ALA THR GLN

AAC CAG TAC GAT GAG TTT GAC ATC GAC TGC GAC AAC CTG AGC TAC ATG CCC ACT GTG GTC
ASN GLN TYR ASP GLU PHE ASP ILE ASP CYS ASP ASN LEU SER TYR MET PRO THR VAL VAL

TTT GAG ATC AAT GGC AAA ATG TAC CCA CTG ACC CCC TCC GCC TAT ACC AGC CAG GAC CAG
PHE GLU ILE ASN GLY LYS MET TYR PRO LEU THR PRO SER ALA TYR THR SER GLN ASP GLN

GGC TTC TGT ACC AGT GGC TTC CAG AGT GAA AAT CAT TCC CAG AAA TGG ATC CTG GGG GAT
GLY PHE CYS THR SER GLY PHE GLN SER GLU ASN HIS SER GLN LYS TRP ILE LEU GLY ASP

GTT TTC ATC CGA GAG TAT TAC AGC GTC TTT GAC AGG GCC AAC AAC CTC GTG GGG CTG GCC
VAL PHE ILE ARG GLU TYR TYR SER VAL PHE ASP ARG ALA ASN ASN LEU VAL GLY LEU ALA

AAA GCC ATC TGA
LYS ALA ILE.
```

4. A pre-prorennin signal sequence coding for sixteen amino acids including an initiator ATG codon comprising nucleotides 205–252 of Table 1. This sequence directs the secretion of pre-prorennin from stomach cells which synthesize it, and hence it is believed useful when attached to other cloned genes for directing secretion of their protein products out of host cells into a periplasmic space or into culture media. In addition, these extra nucleotides, not required for rennin activity, when translated into amino acids may play a role in stabilizing the enzyme against proteolytic degradation while it is inside the cell. This could be of general usefulness for stabilizing the clone gene products in various host cells and in shelf items.

5. A "pro" or zymogen sequence at nucleotide Nos. 253–378 in Table 1 which is a sequence of 126 nucleotides coding for 42 amino acids which form the zymogen portion of the prorennin molecule. This sequence forms the inactive zymogen of rennin and is removed to generate active rennin. The inactive zymogen can have long shelf life. It may also stabilize the rennin molecule and thus may be of general usefulness for stabilizing gene products of other cloned genes.

As used herein, the term "genetic material derived from recombinant DNA material" indicates the genetic material of the host cells which have been transformed with recombinant DNA and cloned to obtain cells which carry the genetic information for the desired product. Recombinant DNA material is used in its normal sense to denote DNA derived from two or more different sources joined or spliced together to form a single molecule but also includes synthesized DNA obtained for example by chemical synthesis. Obviously the recombinant methods used to isolate and obtain the original recombinant DNA material may produce host cells which are then cloned and grown without the need for reuse of genetic recombinant methods. In such case, the cloned cells are considered to be derived from the cells which were originally treated by recombinant DNA methods and are considered to contain genetic material derived from recombinant DNA material.

As described above, recombinant DNA molecules are formed comprising genes coding for at least one polypeptide displaying milk clotting activity or useful in producing such polypeptides.

Although specific prorennin, pre-prorennin and rennin genes are specifically set forth in Table 1, it should be understood that these terms as used herein include functional equivalents thereof having any changes in nucleotide or amino acid sequences or alterations which do not significantly affect milk clotting or catalytic activity of the final rennin product. Thus the broad term "rennin" as used in rennin, pre-prorennin and prorennin is meant to include any sequence of amino acids that clots mammalian milk such as bovine or goat's milk, and thus may include selected fragments of rennin as previously sequenced in the prior art. The rennin, pre-prorennin and prorennin can have non-functional amino acid sequences attached thereto which can be removed by conventional methods to enhance the desired activity of the polypeptide.

As mentioned above, calf rennin exists in two allelic forms A and B which differ at the 290 amino acid sequence position and possibly at the 204 position. Although the cloning and expression of rennin A is described here, a gene for rennin B may be readily generated from the A form gene by simple techniques outlined below. Expression of rennin B may be obtained in a manner identical to that described here for the A form. In order to generate a gene for rennin B, oligonucleotides spanning the regions which are to be changed and including the desired changes could be chemically synthesized. For example, two 20-mer oligonucleotides, one of sequence identical to nucleotides 847–866 (Table 1) except nucleotide 856 is changed from a A to a G, and one of sequence identical to nucleotides 1099–1118 (Table 1) except nucleotide 1109 is changed from A to G, would be synthesized and used to prime second strand DNA synthesis off of f1 phage 293-118/37 double-stranded DNA which had been randomly nicked and converted to single strands with endonuclease III by the method of R. B. Wallace et al (*Science* [1980] 209 1396–1400). The resulting double-stranded circular DNA would be ligated with $T_4$ DNA polymerase and used to transform an appropriate *E. coli* strain. A mixture of phages will result, some carrying the gene for rennin A and some carrying the modified rennin A gene bearing one or the other of the two specified changes. DNA sequencing of the relevant restriction fragments will allow selection of phage carrying each desired changes and a complete rennin B gene may be generated by splicing the two together at an appropriate restriction site. If the rennin A to be converted to rennin B differs from rennin B only at the 290 position, then only the synthetic oligonucleotide spanning the region 1099 to 1118 need be used and the sequence for 847–866 is not used.

Although the methods of this invention described starting with RNA material it is also possible to start by isolating the gene derived from the genomic DNA. In that case the intervening sequences would be first spliced out or a suitable host organism would be used which is capable of processing the RNA to remove intervening sequences. It is also possible to start by chemically synthesizing the appropriate RNA or DNA, or portions thereof, and then employing procedures described herein ultimately to obtain the expression of either rennin, pre-prorennin and/or prorennin. Furthermore, cloned genes for the milk-clotting proteins of other organisms, such as sheep, goat, pig or water buffalo, which may produce rennin-like enzymes can be generated using the procedures described here.

What is claimed is:

1. A transformed living cell selected from the group consisting of yeast and bacteria, containing genetic material derived from recombinant DNA material coding for bovine rennin.

2. A transformed living cell according to claim 1 wherein the cell is a bacterium.

3. A transformed living cell according to claim 2 wherein the bacterium is *Escherichia coli.*

4. A transformed living cell according to claim 1 wherein the cell is a yeast.

5. A transformed living cell according to claim 4 wherein the yeast is *Saccharomyces cerevisiae.*

6. A transformed living cell selected from the group consisting of yeast and bacteria, containing genetic material derived from recombinant DNA material coding for bovine pre-prorennin.

7. A transformed living cell according to claim 2 wherein the cell is a bacterium.

8. A transformed living cell according to claim 7 wherein the bacterium is *Escherichia coli.*

9. A transformed living cell according to claim 6 wherein the cell is a yeast.

10. A transformed living cell according to claim 9 wherein the yeast is *Saccharomyces cerevisiae.*

11. A transformed living cell selected from the group consisting of yeast and bacteria, containing genetic material derived from recombinant DNA material coding for bovine prorennin.

12. A transformed living cell according to claim 11 wherein the cell is a bacterium.

13. A transformed living cell according to claim 12 wherein the bacterium is *Escherichia coli.*

14. A transformed living cell according to claim 11 wherein the cell is a yeast.

15. A transformed living cell according to claim 14 wherein the yeast is *Saccharomyces cerevisiae.*

16. A prorennin gene comprising a nucleotide sequence coding for the amino acid sequence of bovine prorennin and excluding any intervening nucleotide sequences present in bovine genomic DNA encoding prorennin.

17. A prorennin gene in accordance with claim 16 and having operatively attached thereto a vector which replicates in a suitable host cell.

18. A bovine pre-prorennin gene comprising a nucleotide sequence coding for the amino acid sequence of pre-prorennin and excluding any intervening nucleotide sequences present in bovine genomic DNA encoding pre-prorennin.

19. A pre-prorennin gene in accordance with claim 18 and having operatively attached thereto a vector with replicates in a suitable host cell.

20. A process for producing preprorennin prorennin, or rennin, which comprises introducing a recombinant plasmid into a microorganism, culturing the microorganism under such conditions that it produces the desired preprorennin, prorennin, or rennin, respectively, and collecting the preprorennin prorennin, or rennin respectively, wherein the plasmid comprises a structural gene coding for preprorennin as claimed in claim 16.

21. A rennin gene comprising a nucleotide sequence coding for the amino acid sequence of bovine rennin and excluding any intervening nucleotide sequences present in bovine genomic DNA encoding rennin.

22. A rennin gene in accordance with claim 21 and having operatively attached thereto a vector which replicates in a suitable host cell.

23. Recombinant DNA material found in *E. coli* American Type Culture Collection Accession number 31929.

24. Recombinant DNA material found in *Saccharomyces cerevisiae* American Type Culture Collection Accession number 20623.

25. Recombinant DNA material comprising prorennin nucleotide sequence

```
GCT GAG ATC ACC AGG ATC CCT CTG TAC AAA GGC AAG TCT CTG AGG AAG GCG CTG AAG GAG CAT
ALA GLU ILE THR ARG ILE PRO LEU TYR LYS GLY LYS SER LEU ARG LYS ALA LEU LYS GLU HIS

GGG CTT CTG GAG GAC TTC CTG CAG AAA CAG CAG TAT GGC ATC AGC AGC AAG TAC TCC GGC TTC
GLY LEU LEU GLU ASP PHE LEU GLN LYS GLN GLN TYR GLY ILE SER SER LYS TYR SER GLY PHE

GGG GAG GTG GCC AGC GTG CCC CTG ACC AAC TAC CTG GAT AGT CAG TAC TTT GGG AAG ATC
GLY GLU VAL ALA SER VAL PRO LEU THR ASN TYR LEU ASP SER GLN TYR PHE GLY LYS ILE

TAC CTC GGG ACC CCG CCC CAG GAG TTC ACC GTG CTG TTT GAC ACT GGC TCC TCT GAC TTC
TYR LEU GLY THR PRO PRO GLN GLU PHE THR VAL LEU PHE ASP THR GLY SER SER ASP PHE

TGG GTA CCC TCT ATC TAC TGC AAG AGC AAT GCC TGC AAA AAC CAC CAG CGC TTC GAC CCG
TRP VAL PRO SER ILE TYR CYS LYS SER ASN ALA CYS LYS ASN HIS GLN ARG PHE ASP PRO

AGA AAG TCG TCC ACC TTC CAG AAC CTG GGC AAG CCC CTG TCT ATC CAC TAC GGG ACA GGC
ARG LYS SER SER THR PHE GLN ASN LEU GLY LYS PRO LEU SER ILE HIS TYR GLY THR GLY

AGC ATG CAG GGC ATC CTG GGC TAT GAC ACC GTC ACT GTC TCC AAC ATT GTG GAC ATC CAG
SER MET GLN GLY ILE LEU GLY TYR ASP THR VAL THR VAL SER ASN ILE VAL ASP ILE GLN

CAG ACA GTA GGC CTG AGC ACC CAG GAG CCC GGG GAC GTC TTC ACC TAT GCC GAA TTC GAC
GLN THR VAL GLY LEU SER THR GLN GLU PRO GLY ASP VAL PHE THR TYR ALA GLU PHE ASP

GGG ATC CTG GGG ATG GCC TAC CCC TCG CTC GCC TCA GAG TAC TCG ATA CCC GTG TTT GAC
GLY ILE LEU GLY MET ALA TYR PRO SER LEU ALA SER GLU TYR SER ILE PRO VAL PHE ASP

AAC ATG ATG AAC AGG CAC CTG GTG GCC CAA GAC CTG TTC TCG GTT TAC ATG GAC AGG AAT
ASN MET MET ASN ARG HIS LEU VAL ALA GLN ASP LEU PHE SER VAL TYR MET ASP ARG ASN

GGC CAG GAG AGC ATG CTC ACG CTG GGG GCC ATC GAC CCG TCC TAC TAC ACA GGG TCC CTG
GLY GLN GLU SER MET LEU THR LEU GLY ALA ILE ASP PRO SER TYR TYR THR GLY SER LEU
```

```
CAC TGG GTG CCC GTG ACA GTG CAG CAG TAC TGG CAG TTC ACT GTG GAC AGT GTC ACC ATC
HIS TRP VAL PRO VAL THR VAL GLN GLN TYR TRP GLN PHE THR VAL ASP SER VAL THR ILE

AGC GGT GTG GTT GTG GCC TGT GAG GGT GGC TGT CAG GCC ATC CTG GAC ACG GGC ACC TCC
SER GLY VAL VAL VAL ALA CYS GLU GLY GLY CYS GLN ALA ILE LEU ASP THR GLY THR SER

AAG CTG GTC GGG CCC AGC AGC GAC ATC CTC AAC ATC CAG CAG GCC ATT GGA GCC ACA CAG
LYS LEU VAL GLY PRO SER SER ASP ILE LEU ASN ILE GLN GLN ALA ILE GLY ALA THR GLN

AAC CAG TAC GAT GAG TTT GAC ATC GAC TGC GAC AAC CTG AGC TAC ATG CCC ACT GTG GTC
ASN GLN TYR ASP GLU PHE ASP ILE ASP CYS ASP ASN LEU SER TYR MET PRO THR VAL VAL

TTT GAG ATC AAT GGC AAA ATG TAC CCA CTG ACC CCC TCC GCC TAT ACC AGC CAG GAC CAG
PHE GLU ILE ASN GLY LYS MET TYR PRO LEU THR PRO SER ALA TYR THR SER GLN ASP GLN

GGC TTC TGT ACC AGT GGC TTC CAG AGT GAA AAT CAT TCC CAG AAA TGG ATC CTG GGG GAT
GLY PHE CYS THR SER GLY PHE GLN SER GLU ASN HIS SER GLN LYS TRP ILE LEU GLY ASP

GTT TTC ATC CGA GAG TAT TAC AGC GTC TTT GAC AGG GCC AAC AAC CTC GTG GGG CTG GCC
VAL PHE ILE ARG GLU TYR TYR SER VAL PHE ASP ARG ALA ASN ASN LEU VAL GLY LEU ALA

AAA GCC ATC TGA
LYS ALA ILE.
```

26. Recombinant DNA material comprising pre-prorennin nucleotide sequence

```
                    ATG AGG TGT CTC GTG GTG CTA CTT GCT GTC TTC GCT CTC TCC CAG GGC
                    MET ARG CYS LEU VAL VAL LEU LEU ALA VAL PHE ALA LEU SER GLN GLY

GCT GAG ATC ACC AGG ATC CCT CTG TAC AAA GGC AAG TCT CTG AGG AAG GCG CTG AAG GAG CAT
ALA GLU ILE THR ARG ILE PRO LEU TYR LYS GLY LYS SER LEU ARG LYS ALA LEU LYS GLU HIS

GGG CTT CTG GAG GAC TTC CTG CAG AAA CAG CAG TAT GGC ATC AGC AGC AAG TAC TCC GGC TTC
GLY LEU LEU GLU ASP PHE LEU GLN LYS GLN GLN TYR GLY ILE SER SER LYS TYR SER GLY PHE

GGG GAG GTG GCC AGC GTG CCC CTG ACC AAC TAC CTG GAT AGT CAG TAC TTT GGG AAG ATC
GLY GLU VAL ALA SER VAL PRO LEU THR ASN TYR LEU ASP SER GLN TYR PHE GLY LYS ILE

TAC CTC GGG ACC CCG CCC CAG GAG TTC ACC GTG CTG TTT GAC ACT GGC TCC TCT GAC TTC
TYR LEU GLY THR PRO PRO GLN GLU PHE THR VAL LEU PHE ASP THR GLY SER SER ASP PHE

TGG GTA CCC TCT ATC TAC TGC AAG AGC AAT GCC TGC AAA AAC CAC CAG CGC TTC GAC CCG
TRP VAL PRO SER ILE TYR CYS LYS SER ASN ALA CYS LYS ASN HIS GLN ARG PHE ASP PRO

AGA AAG TCG TCC ACC TTC CAG AAC CTG GGC AAG CCC CTG TCT ATC CAC TAC GGG ACA GGC
ARG LYS SER SER THR PHE GLN ASN LEU GLY LYS PRO LEU SER ILE HIS TYR GLY THR GLY

AGC ATG CAG GGC ATC CTG GGC TAT GAC ACC GTC ACT GTC TCC AAC ATT GTG GAC ATC CAG
SER MET GLN GLY ILE LEU GLY TYR ASP THR VAL THR VAL SER ASN ILE VAL ASP ILE GLN

CAG ACA GTA GGC CTG AGC ACC CAG GAG CCC GGG GAC GTC TTC ACC TAT GCC GAA TTC GAC
GLN THR VAL GLY LEU SER THR GLN GLU PRO GLY ASP VAL PHE THR TYR ALA GLU PHE ASP

GGG ATC CTG GGG ATG GCC TAC CCC TCG CTC GCC TCA GAG TAC TCG ATA CCC GTG TTT GAC
GLY ILE LEU GLY MET ALA TYR PRO SER LEU ALA SER GLU TYR SER ILE PRO VAL PHE ASP

AAC ATG ATG AAC AGG CAC CTG GTG GCC CAA GAC CTG TTC TCG GTT TAC ATG GAC AGG AAT
ASN MET MET ASN ARG HIS LEU VAL ALA GLN ASP LEU PHE SER VAL TYR MET ASP ARG ASN

GGC CAG GAG AGC ATG CTC ACG CTG GGG GCC ATC GAC CCG TCC TAC TAC ACA GGG TCC CTG
GLY GLN GLU SER MET LEU THR LEU GLY ALA ILE ASP PRO SER TYR TYR THR GLY SER LEU

CAC TGG GTG CCC GTG ACA GTG CAG CAG TAC TGG CAG TTC ACT GTG GAC AGT GTC ACC ATC
HIS TRP VAL PRO VAL THR VAL GLN GLN TYR TRP GLN PHE THR VAL ASP SER VAL THR ILE

AGC GGT GTG GTT GTG GCC TGT GAG GGT GGC TGT CAG GCC ATC CTG GAC ACG GGC ACC TCC
SER GLY VAL VAL VAL ALA CYS GLU GLY GLY CYS GLN ALA ILE LEU ASP THR GLY THR SER

AAG CTG GTC GGG CCC AGC AGC GAC ATC CTC AAC ATC CAG CAG GCC ATT GGA GCC ACA CAG
LYS LEU VAL GLY PRO SER SER ASP ILE LEU ASN ILE GLN GLN ALA ILE GLY ALA THR GLN

AAC CAG TAC GAT GAG TTT GAC ATC GAC TGC GAC AAC CTG AGC TAC ATG CCC ACT GTG GTC
ASN GLN TYR ASP GLU PHE ASP ILE ASP CYS ASP ASN LEU SER TYR MET PRO THR VAL VAL

TTT GAG ATC AAT GGC AAA ATG TAC CCA CTG ACC CCC TCC GCC TAT ACC AGC CAG GAC CAG
PHE GLU ILE ASN GLY LYS MET TYR PRO LEU THR PRO SER ALA TYR THR SER GLN ASP GLN

GGC TTC TGT ACC AGT GGC TTC CAG AGT GAA AAT CAT TCC CAG AAA TGG ATC CTG GGG GAT
GLY PHE CYS THR SER GLY PHE GLN SER GLU ASN HIS SER GLN LYS TRP ILE LEU GLY ASP
```

```
GTT TTC ATC CGA GAG TAT TAC AGC GTC TTT GAC AGG GCC AAC AAC CTC GTG GGG CTG GCC
VAL PHE ILE ARG GLU TYR TYR SER VAL PHE ASP ARG ALA ASN ASN LEU VAL GLY LEU ALA

AAA GCC ATC TGA
LYS ALA ILE.
```

27. A process for producing preprorennin prorennin, or rennin, which comprises introducing a recombinant plasmid into a microorganism, culturing the microorganism under such conditions that it produces the desired preprorennin, prorennin, or rennin, respectively, and collecting the preprorennin, prorennin, or rennin, respectively, wherein the plasmid comprises a structural coding gene for preprorennin as claimed in claim 26.

28. Recombinant DNA material comprising rennin nucleotide sequence

30. Recombinant DNA material coding for a polypeptide zymogen sequence and having the following nucleotide and polypeptide sequence or other nucleotide sequence coding the said polypeptide

```
GGG GAG GTG GCC AGC GTG CCC CTG ACC AAC TAC CTG GAT AGT CAG TAC TTT GGG AAG ATC
GLY GLU VAL ALA SER VAL PRO LEU THR ASN TYR LEU ASP SER GLN TYR PHE GLY LYS ILE

TAC CTC GGG ACC CCG CCC CAG GAG TTC ACC GTG CTG TTT GAC ACT GGC TCC TCT GAC TTC
TYR LEU GLY THR PRO PRO GLN GLU PHE THR VAL LEU PHE ASP THR GLY SER SER ASP PHE

TGG GTA CCC TCT ATC TAC TGC AAG AGC AAT GCC TGC AAA AAC CAC CAG CGC TTC GAC CCG
TRP VAL PRO SER ILE TYR CYS LYS SER ASN ALA CYS LYS ASN HIS GLN ARG PHE ASP PRO

AGA AAG TCG TCC ACC TTC CAG AAC CTG GGC AAG CCC CTG TCT ATC CAC TAC GGG ACA GGC
ARG LYS SER SER THR PHE GLN ASN LEU GLY LYS PRO LEU SER ILE HIS TYR GLY THR GLY

AGC ATG CAG GGC ATC CTG GGC TAT GAC ACC GTC ACT GTC TCC AAC ATT GTG GAC ATC CAG
SER MET GLN GLY ILE LEU GLY TYR ASP THR VAL THR VAL SER ASN ILE VAL ASP ILE GLN

CAG ACA GTA GGC CTG AGC ACC CAG GAG CCC GGG GAC GTC TTC ACC TAT GCC GAA TTC GAC
GLN THR VAL GLY LEU SER THR GLN GLU PRO GLY ASP VAL PHE THR TYR ALA GLU PHE ASP

GGG ATC CTG GGG ATG GCC TAC CCC TCG CTC GCC TCA GAG TAC TCG ATA CCC GTG TTT GAC
GLY ILE LEU GLY MET ALA TYR PRO SER LEU ALA SER GLU TYR SER ILE PRO VAL PHE ASP

AAC ATG ATG AAC AGG CAC CTG GTG GCC CAA GAC CTG TTC TCG GTT TAC ATG GAC AGG AAT
ASN MET MET ASN ARG HIS LEU VAL ALA GLN ASP LEU PHE SER VAL TYR MET ASP ARG ASN

GGC CAG GAG AGC ATG CTC ACG CTG GGG GCC ATC GAC CCG TCC TAC TAC ACA GGG TCC CTG
GLY GLN GLU SER MET LEU THR LEU GLY ALA ILE ASP PRO SER TYR TYR THR GLY SER LEU

CAC TGG GTG CCC GTG ACA GTG CAG CAG TAC TGG CAG TTC ACT GTG GAC AGT GTC ACC ATC
HIS TRP VAL PRO VAL THR VAL GLN GLN TYR TRP GLN PHE THR VAL ASP SER VAL THR ILE

AGC GGT GTG GTT GTG GCC TGT GAG GGT GGC TGT CAG GCC ATC CTG GAC ACG GGC ACC TCC
SER GLY VAL VAL VAL ALA CYS GLU GLY GLY CYS GLN ALA ILE LEU ASP THR GLY THR SER

AAG CTG GTC GGG CCC AGC AGC GAC ATC CTC AAC ATC CAG CAG GCC ATT GGA GCC ACA CAG
LYS LEU VAL GLY PRO SER SER ASP ILE LEU ASN ILE GLN GLN ALA ILE GLY ALA THR GLN

AAC CAG TAC GAT GAG TTT GAC ATC GAC TGC GAC AAC CTG AGC TAC ATG CCC ACT GTG GTC
ASN GLN TYR ASP GLU PHE ASP ILE ASP CYS ASP ASN LEU SER TYR MET PRO THR VAL VAL

TTT GAG ATC AAT GGC AAA ATG TAC CCA CTG ACC CCC TCC GCC TAT ACC AGC CAG GAC CAG
PHE GLU ILE ASN GLY LYS MET TYR PRO LEU THR PRO SER ALA TYR THR SER GLN ASP GLN

GGC TTC TGT ACC AGT GGC TTC CAG AGT GAA AAT CAT TCC CAG AAA TGG ATC CTG GGG GAT
GLY PHR CYS THR SER GLY PHE GLN SER GLU ASN HIS SER GLN LYS TRP ILE LEU GLY ASP

GTT TTC ATC CGA GAG TAT TAC AGC GTC TTT GAC AGG GCC AAC AAC CTC GTG GGG CTG GCC
VAL PHE ILE ARG GLU TYR TYR SER VAL PHE ASP ARG ALA ASN ASN LEU VAL GLY LEU ALA

AAA GCC ATC TGA
LYS ALA ILE.
```

29. Recombinant DNA material coding for a polypeptide signal sequence and having the following nucleotide and polypeptide sequence or other nucleotide sequence coding the said polypeptide.

```
ATG AGG TGT CTC GTG GTG CTA CTT GCT GTC TTC GCT CTC TCC CAG GGC
MET ARG CYS LEU VAL VAL LEU LEU ALA VAL PHE ALA LEU SER GLN GLY.
```

```
GCT GAG ATC ACC AGG ATC CCT CTG TAC AAA GGC AAG TCT CTG AGG AAG GCG CTG AAG GAG CAT
ALA GLU ILE THR ARG ILE PRO LEU TYR LYS GLY LYS SER LEU ARG LYS ALA LEU LYS GLU HIS

GGG CTT CTG GAG GAC TTC CTG CAG AAA CAG CAG TAT GGC ATC AGC AGC AAG TAC TCC GGC TTC
GLY LEU LEU GLU ASP PHE LEU GLN LYS GLN GLN TYR GLY ILE SER SER LYS TYR SER GLY PHE.
```

31. A transformed fungal living cell containing genetic material derived from recombinant DNA material coding for bovine rennin.

32. A transformed fungal living cell containing genetic material derived from recombinant DNA material coding for bovine pre-prorennin.

33. A transformed fungal living cell containing genetic material derived from recombinant DNA material coding for bovine prorennin.

34. A process for producing preprorennin, prorennin, or rennin, comprising, introducing a plasmid into a microorganism, culturing the microorganism under conditions such that it produces the desired preprorennin, prorennin, or rennin, respectively, and collecting the preprorennin, prorennin, or rennin, respectively, wherein the plasmid comprises a gene comprising a nucleotide sequence coding for the amino acid sequence of bovine preprorennin, prorennin, or rennin and excluding any intervening nucleotide sequences present in genomic DNA encoding preprorennin, prorennin, or rennin.

* * * * *